United States Patent
Aloup et al.

[11] Patent Number: 5,990,108
[45] Date of Patent: Nov. 23, 1999

[54] 5H,10H-IMIDAZO[1,2-A]INDENO[1,2-E] PYRAZINE-4-ONE DERIVATIVES, PREPARATION THEREOF, INTERMEDIATES THEREOF AND DRUGS CONTAINING THE SAME

[75] Inventors: Jean-Claude Aloup, Villeneuve-le-Roi; Jean Bouquerel, Drancy; Dominique Damour, Orly; Jean-Claude Hardy, Cergy-Saint-Christophe; Patrick Jimonet, Villepreux; Franco Manfre, Limeil-Brevannes; Serge Mignani, Chatenay-Malabry; Patrick Nemecek, Thiais, all of France

[73] Assignee: Rhône Poulenc Rorer S.A., Antony, France

[21] Appl. No.: 09/101,428

[22] PCT Filed: Jan. 6, 1997

[86] PCT No.: PCT/FR97/00019

§ 371 Date: Jul. 9, 1998

§ 102(e) Date: Jul. 9, 1998

[87] PCT Pub. No.: WO97/25328

PCT Pub. Date: Jul. 17, 1997

[30] Foreign Application Priority Data

Jan. 10, 1996 [FR] France ..................... 96 00192

[51] Int. Cl.⁶ ........................ A61K 31/495; C07D 487/04
[52] U.S. Cl. ............................ 514/250; 544/343
[58] Field of Search .............................. 544/343; 514/250

[56] References Cited

FOREIGN PATENT DOCUMENTS

WO 95/26349   10/1995   WIPO .
WO 96/31511   10/1996   WIPO .

*Primary Examiner*—Robert Gerstl
*Attorney, Agent, or Firm*—Finnegan, Henderson, Farabow, Garrett & Dunner, L.L.P.

[57] ABSTRACT

Compounds of formula (I), wherein R is a hydrogen atom or a —COOH, -alk-COOH, —PO₃H₂, —CH₂—PO₃H₂, or —CH=CH—COOH radical, or a phenyl radical substituted by a carboxy radical, R₁ is an alk-CN, -alk-COOH, -alk-Het, alk-PO₃H₂ or -alk-CO—NH—SO₂R₂ radical, R₂ is an alkyl or phenyl radical, alk is an alkyl radical, Het is a saturated or unsaturated mono- or polycyclic heterocyclic ring containing 1–9 carbon atoms and one or more heteroatoms selected from O, S and N, said heterocyclic ring optionally being substituted by one or more alkyl, phenyl or phenylalkyl radicals, with the proviso that when R is a hydrogen atom or a —COOH or —PO₃H₂ radical, R₁ cannot be -alk-COOH, isomers, racemic mixtures, enantiomers and diastereoisomers thereof, salts thereof, the preparation thereof, intermediates thereof and drugs containing said compounds, are disclosed. The compounds of formula (I) have valuable pharmacological properties and are antagonists of the α-amino-3-hydroxy-5-methyl-4-isoxazolepropionic acid (AMPA) receptor also known as the quisqualate receptor. Furthermore, the compounds of formula (I) are non-competitive antagonists of the N-methyl-D-aspartate (NMDA) receptor, and specifically ligands for NMDA receptor glycine modulator sites.

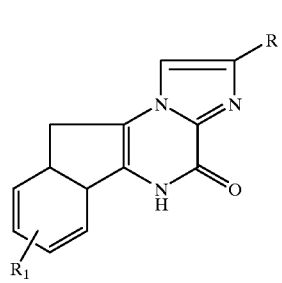

(I)

10 Claims, No Drawings

5H,10H-IMIDAZO[1,2-A] INDENO[1,2-E] PYRAZINE-4-ONE DERIVATIVES, PREPARATION THEREOF, INTERMEDIATES THEREOF AND DRUGS CONTAINING THE SAME

The present invention relates to the compounds of formula:

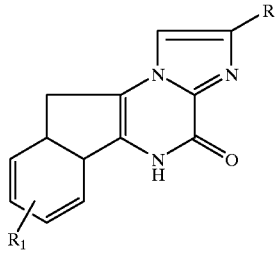

(I)

their isomers, their racemates, enantiomers and diastereoisomers, their salts, their preparation, their intermediates and the medicaments containing them.

In the formula (I),

R represents a hydrogen atom or a —COOH radical, an -alk-COOH radical, a —PO$_3$H$_2$ radical, —CH$_2$—PO$_3$H$_2$ radical, a —CH=CH—COOH radical or a phenyl radical substituted with a carboxyl radical, R$_1$ represents an -alk-CN, -alk-COOH, -alk-Het, -alk-PO$_3$H$_2$ or -alk-CO—NH—SO$_2$R$_2$ radical, R$^2$ represents an alkyl or phenyl radical, alk represents an alkyl radical, Het represents a saturated or unsaturated mono- or polycyclic heterocycle containing 1 to 9 carbon atoms and one or more heteroatoms chosen from O, S, N, the heterocycle being optionally substituted with one or more alkyl, phenyl or phenylalkyl radicals, it being understood that when R represents a hydrogen atom or a —COOH or —PO$_3$H$_2$ radical, R$_1$ cannot represent -alk-COOH.

Unless otherwise stated, in the preceding definitions and in those which follow, the alkyl or alkoxy radicals contain 1 to 6 carbon atoms in a straight or branched chain.

Preferably, the substituent R$_1$ is at position 8 or 9.

Preferably, Het represents a tetrazol-5-yl ring.

The compounds of formula (I) for which R represents a —CH=CH—COOH radical have isomeric forms (E and Z). These isomers and mixtures thereof form part of the invention.

The racemates, enantiomers and diastereoisomers of the compounds of formula (I) for which R represents an -alk-COOH radical and/or R$_1$ represents an -alk-CN, -alk-COOH, -alk-Het, -alk-PO$_3$H$_2$ or -alk-CO—NH—SO$_2$R$_2$ radical also form part of the invention.

The compounds of formula (I) can be prepared by cyclization, either in the presence of ammonium acetate, or in the presence of ammonia, or in the presence of ammonium acetate and ammonia, of a derivative of formula:

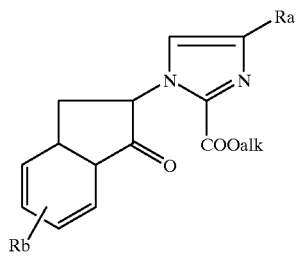

(II)

in which Ra represents a hydrogen atom or a -COOalk radical, an -alk-COOalk' radical, a —PO(Oalk)$_2$ radical, a —CH$_2$—PO(Oalk)$_2$ radical, a —CH=CH—COOalkl radical or a phenyl radical substituted with an alkoxycarbonyl radical, Rb represents an -alk-CN, -alk-COOalk', -alk-PO (Oalk')$_2$, -alk-CO—NH—SO$_2$R$_2$ or -alk-Het radical, alk and alk' represent an alkyl radical, R$_2$ and Het have the same meanings as in the formula (I), followed by a hydrolysis.

When Het represents a tetrazolyl-5-yl radical, it is preferable to use a derivative of formula (II) for which Rb represents an -alk-tetrazol-5-yl radical in which the tetrazole is substituted at position 1 or 2 with a benzyl radical and then to debenzylate the final product.

This cyclization is carried out preferably in an organic acid such as acetic acid, at the boiling temperature of the reaction medium, optionally in the presence of ammonia in solution in a lower aliphatic alcohol such as methanol. The hydrolysis of the —COOalk and —PO(Oalk)$_2$ functional groups and the debenzylation are carried out by any known method which makes it possible to go from an ester to the corresponding acid or from a dialkylphosphonate to the corresponding phosphonic acid or to debenzylate without modifying the rest of the molecule. Preferably, the procedure is carried out by means of an inorganic acid such as hydrobromic acid or hydrochloric acid, at a temperature of 100° C.

The derivatives of formula (II) can be obtained by the action of an indanone of formula:

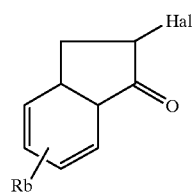

(III)

in which Rb has the same meanings as in the formula (II) or represents an -alk-Het' radial for which Het' represents a tetrazol-5-yl radical substituted at position 1 or 2 with a benzyl radical and Hal represents a halogen atom (preferably chlorine or bromine), on a derivative of formula:

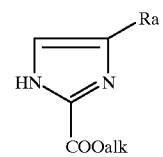

(IV)

in which Ra has the same meanings as in the formula (II) and alk represents an alkyl radical.

This reaction is generally carried out in an inert solvent such as an alcohol (for example methanol or ethanol), a ketone (for example acetone), an aromatic hydrocarbon (for example toluene), dimethylformamide or in the absence of solvent, optionally in the presence of a base such as sodium hydride or potassium carbonate with, optionally, a crown ether such as 18C6, at a temperature of between 20° C. and the boiling temperature of the reaction medium or the melting temperature of the reaction medium.

The derivatives of formula (II) for which Ra represents a —COOalk radical in which alk is not a tert-butyl radical and Rb represents an -alk-CO—NH—SO$_2$R$_2$ radical in which R$_2$ has the same meanings as in the formula (I) can also be prepared by the action of a derivative of formula (II) for which Ra represents a —COOalk radical in which alk is not a tert-butyl radical and Rb represents an -alk-COOH radical, on a H$_2$N—SO$_2$R$_2$ derivative in which R$_2$ has the same meanings as in the formula (I).

Preferably, an activated derivative of the acid by means of 1,1'-carbonyldiimidazole is used. The procedure is generally carried out when R$_2$ is an alkyl radical, in an inert solvent such as tetrahydrofuran, in the presence of a nitrogenous organic base (for example 1,8-diazabicyclo[5.4.0]undec-7-ene), at a temperature close to 20° C. and when R$_2$ is a phenyl radical, in an inert solvent such as dimethylformamide, in the presence of a base such as an alkali metal hydride (for example sodium hydride), at a temperature of between 0 and 20° C.

The derivatives of formula (II) for which Ra represents a —COOalk radical in which alk is not a tert-butyl radical and Rb represents an -alk-COOH radical can be obtained by selective deesterification of the derivative of formula (II) for which Ra represents a —COOalk radical in which alk is not a tert-butyl radical and Rb represents an -alk-COO-tert-butyl radical.

This reaction is carried out by means of an inorganic acid such as hydrochloric acid, in an inert solvent such as dioxane at a temperature close to 20° C.

The derivatives of formula (III) can be obtained by application or adaptation of the methods described by OLIVIER et. al., Bull. Soc. Chim. France, 3092 (1973), in patent DE 2,640,358 and in the examples. Preferably, the corresponding indanones are halogenated by means of a halogenating agent such as bromine or chlorine, in an inert solvent such as a chlorine-containing solvent (for example methylene chloride or chloroform) or acetic acid, at a temperature close to −15° C. and 20° C., or a copper halide, in dioxane, at a temperature close to 100° C. or by application or adaptation of the methods described by K. MORI, Agr. Biol. Chem., 27 (1), 22 (1963); J. CHAKRAVARTY, Indian J. Chem., 7 (3), 215 (1969), F. G. HOLLIMAN et al. J. Chem. Soc., 9 (1960), D. MUKHOPADHYA et al., J. Indian Chem. Soc., 47 (5), 450 (1970), in patents DE 2,640,358, EP 346,107 and in the examples.

The corresponding indanones can be obtained by application or adaptation of the methods described in the examples. In particular, the indanones substituted on the aromatic ring with an -alk-COOalk', -alk-CN or -alk-Het radical, alk and alk' being alkyl radicals, can be prepared according to the following reaction scheme:

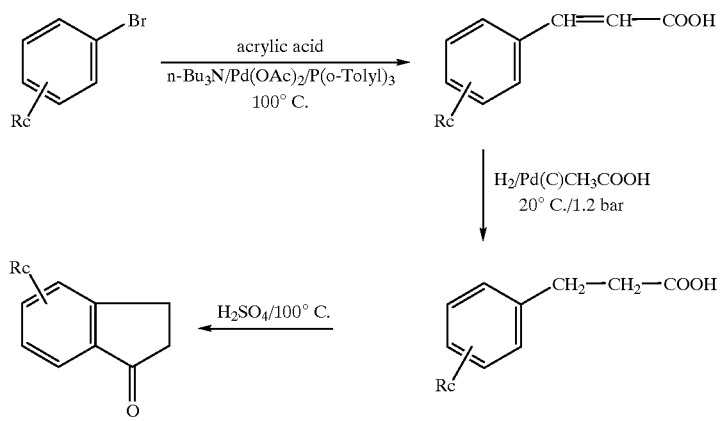

in these formulae, Rc represents an -alk-COOalk', -alk-CN or -alk-Het radical, alk and alk' representing alkyl radicals. In the case where Rc represents an -alk-COOalk' radical, the process comprises a final additional step of esterification by means of oxalyl chloride and a lower aliphatic alcohol, in dichloromethane, at a temperature of 20° C. The bromobenzenes substituted on the aromatic ring with an -alk-Het radical can be obtained by the action of an organometallic derivative of the heterocycle (for example organolithium or organomagnesium) on bromobenzene substituted on the aromatic ring with an -alk-Br radical, in an ether or dimethylformamide, at a temperature of −70° C. to 25° C. The organometallic derivatives of the heterocycles can be obtained by application or adaptation of the methods described by L. ESTEL et al., J. Heterocyclic Chem., 26, 105 (1989); N. S. NARASIMHAN et al., Synthesis, 957 (1983); A. TURCK et al., Synthesis, 881 (1988); A. J. CLARKE et al., Tetrahedron Lett, 27, 2373 (1974); A. R. KATRITZKY et al., Org. Prep. Procedure Int., 20 (6), 585 (1988); N. FURUKAWA et al., Tetrahedron Lett., 28 (47), 5845 (1987); V. SNIECKUS, Chem. Rev., 90, 879 (1990, L. J. BALDWIN et al., J. Het. Chem., 22 (6), 1667 (1985), G. QUEGUINER et al., Tetrahedron, 42 (8), 2253 (1986), G. QUEGUINER et al., Tetrahedron, 51 (47), 13045 (1995) and M. ISHIKURA et al., Heterocycle, 24 (10), 2793 (1986). The bromobenzenes substituted with -alk-Br can be obtained by application or adaptation of the methods described by H. GILMAN, J. Org. Chem., 30, 325 (1965), C. H. DEPUY, J. Am. Chem. Soc., 79, 3710 (1957), S. A. GLOVER, Tetrahedron, 46 (20), 7247 (1990), J. OKADA, Chem. Pharm. Bull., 31 (9), 3074 (1983) and C. K. BRADSHER, J. Org. Chem., 46, 4600 (1981).

The bromobenzenes substituted with -alk-CN can be obtained by application or adaptation of the methods described by PATAI, The chemistry of the cyano group, Wiley, N.Y., 1970.

The bromobenzenes substituted with -alk-COOalk' can be obtained by application or adaptation of the methods described by LAROCK, Comprehensive Organic Transformations, VCH, New York, 1989.

The indanones substituted on the aromatic ring with an -alk-Het radical for which Het represents a tetrazol-5-yl radical in which the tetrazole is substituted at position 1 or 2 with a benzyl radical, can be obtained according to the following reaction scheme:

in these formulae, Rd represents an -alk-tetrazol-5-yl radical in which the tetrazole is substituted at position 1 or 2 with a benzyl radical and Re represents an -alk-tetrazol-5-yl radical.

The indanones substituted on the aromatic ring with an -alk-PO(Oalk')$_2$ radical can be obtained according to the following reaction scheme:

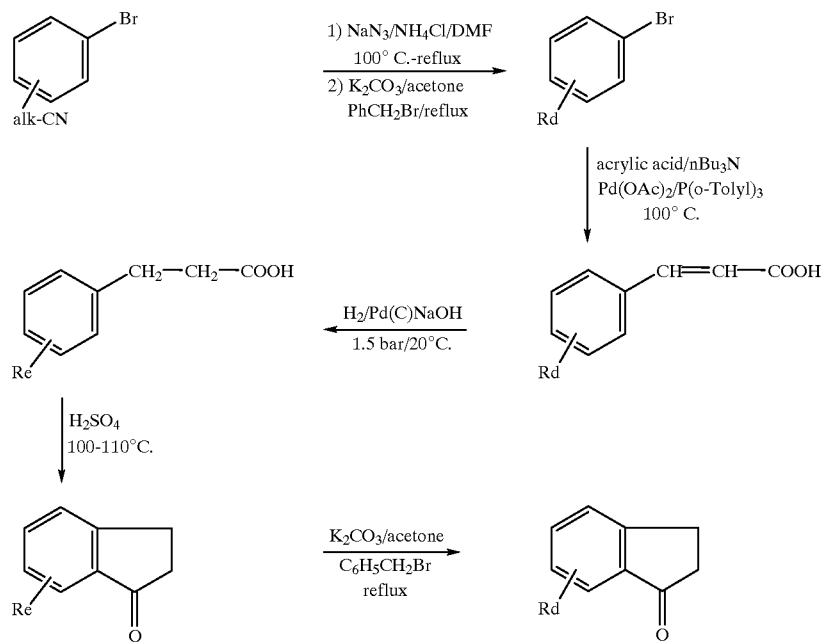

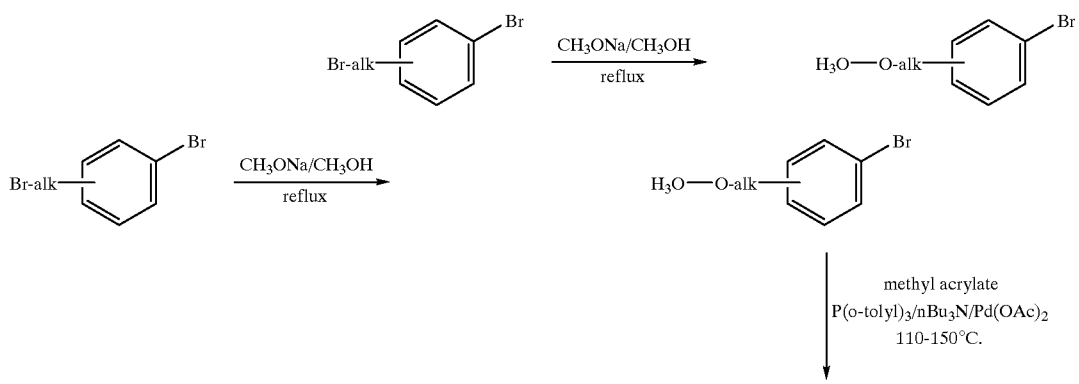

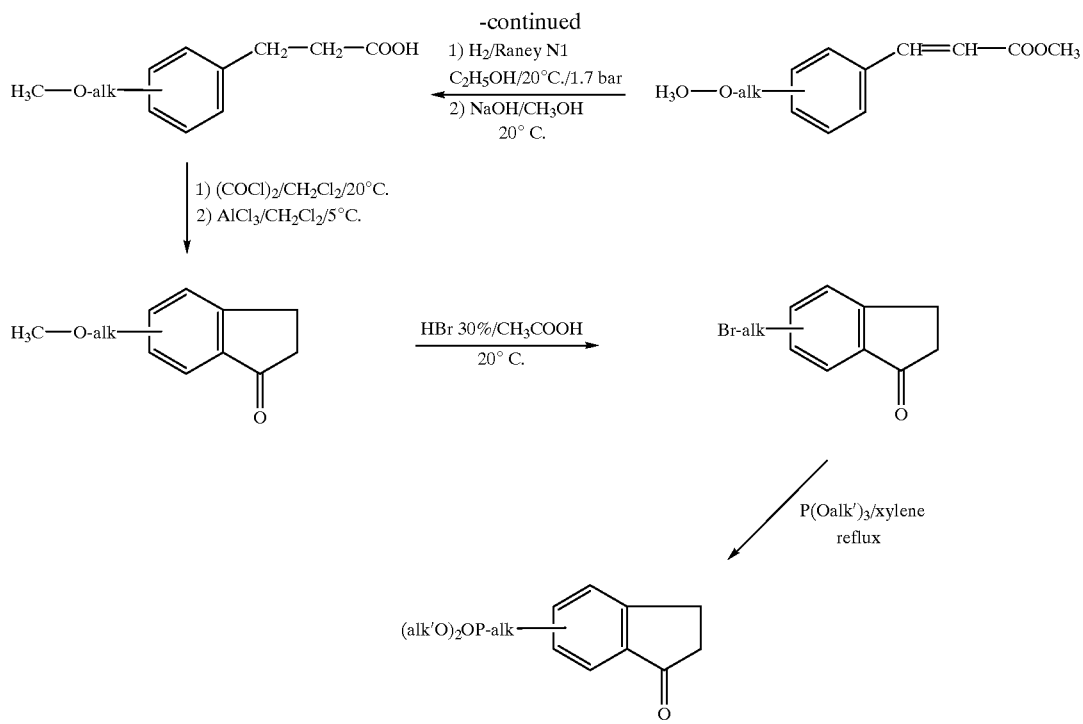

in these formulae, alk and alk' represent alkyl radicals.

The indanones substituted on the aromatic ring by an -alk-CO—NH—SO$_2$R$_2$ radical in which alk represents an alkyl radical and R$_2$ has the same meanings as in the formula (I) can be obtained by condensation of an indanone substituted on the aromatic ring with an -alk-COIm radical for which alk represents an alkyl radical and Im represents an imidazole radical with an R$_2$SO$_2$-NHNa derivative for which R$_2$ has the same meanings as in the formula (I), at a temperature close to 0° C. The indanone substituted on the aromatic ring with an -alk-COIm radical can be obtained by the action of an indanone substituted with an -alk-COOH radical on the carbonylimidazole, in tetrahydrofuran, at a temperature close to 20° C. The R$_2$—SO$_2$-NHNa derivative can be obtained by the action of sodium hydride on a derivative of formula R$_2$—SO$_2$—NH$_2$, in tetrahydrofuran, at a temperature close to 20° C.

The derivatives of formula (IV) for which Ra represents a hydrogen atom or a —COOalk radical can be obtained by application or adaptation of the methods described by P. S. BRANCO et al., Tetrahedron, 48 (30), 6335 (1992) and in U.S. Pat. No. 3,600,399.

The derivatives of formula (IV) for which Ra represents a —PO(Oalk)$_2$ radical can be obtained by the action of an alkyl (hydroxyamino)iminoacetate on a dialkyl ethynylphosphonate in chloroform, at a temperature of between 20 and 50° C. The alkyl (hydroxyamino)iminoacetates can be obtained by application or adaptation of the method described by W. K. WARBURTON, J. Chem. Soc.(C), 1522 (1966) and the dialkyl ethynylphosphonates can be obtained by application or adaptation of the method described in the examples and by D. T. MONAGHAN et al., Brain Res., 278, 138 (1983).

The derivative of formula (IV) for which Ra represents an -alk-COOalk' radical, a —CH$_2$—PO(Oalk)$_2$ radical or a phenyl radical substituted with an alkoxycarbonyl radical are new and form part of the invention as well as their preparation. They can be obtained by the action of H$_2$N— CH$_2$—CO—Rf in the form of a salt with an inorganic acid (for example hydrochloride) in which Rf represents an -alk-COOalk' radical, a —CH$_2$—PO(Oalk)$_2$ radical or a phenyl radical substituted with an alkoxycarbonyl radical on alkOOCC(=NH)—Salk',BF$_4$H, in which alk and alk' represent alkyl radicals, generally in acetic acid, in the presence of sodium acetate, at the boiling temperature of the reaction medium. The H$_2$N—CH$_2$—CO—Rf derivatives in the form of a salt with an inorganic acid (for example hydrochloride) for which Rf represents -alk-COOalk' can be obtained by application or adaptation of the method described by D. E. ORR et al., Chem. Ind. (London), 392 (1983). The H$_2$N—CH$_2$—CO—Rf derivatives in the form of a salt with an inorganic acid (for example hydrochloride) for which Rf represents —CH$_2$—PO(Oalk)$_2$ can be obtained by the action of H$_3$C—PO(Oalk)$_2$ for which alk represents an alkyl radical on H$_2$N-alk-COOH in which the amino functional group is protected for example by a tert-butoxycarbonyl radical and the acid functional group activated for example by 1,1'-carbonyldiimidazole, in the presence of butyllithium, in tetrahydrofuran at a temperature of −75° C. followed by liberation of the amine functional group by means of an inorganic acid such as hydrochloric acid, in dioxane, at a temperature close to 20° C. The H$_2$N—CH$_2$—CO—Rf derivatives for which Rf represents a phenyl substituted with an alkoxycarbonyl radical can be obtained by application or adaptation of the methods described in patent EP52442 or by MINORU SUZUKI, J. Pharm. Soc. Japan, 72, 305 (1952). The alkOOC—C(=NH)—Salk',BF$_4$H derivatives can be obtained by application or adaptation of the method described by H. YAMANAKA et al., Chem. Pharm. Bull., 31 (1), 4549 (1983).

The derivatives of formula (IV) for which Ra represents a —CH=CH—COOalk' or -alk(2C in a straight chain)—COOalk' radical are new and form part of the invention as well as their preparation. They can be obtained according to the following reaction scheme:

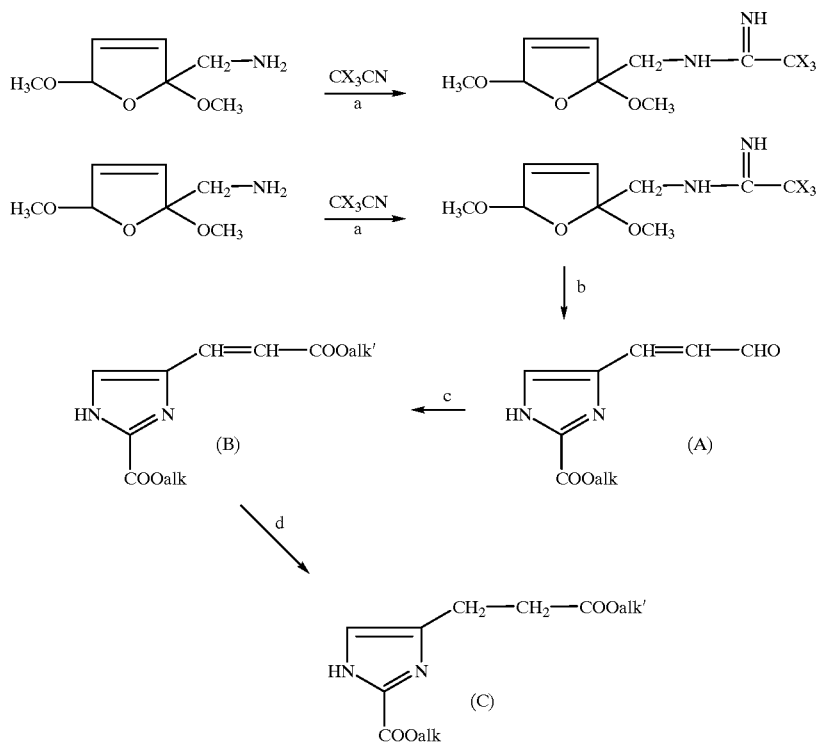

in these formulae alk and alk' represent alkyl radicals and X represents a halogen atom (preferably chlorine or fluorine) or an alkoxy radical.

In step a, the reaction is generally carried out in an inert solvent such as an ether (for example tetrahydrofuran), at a temperature ranging from −78° C. to the boiling temperature of the reaction medium.

In step b, an inorganic or organic acid and then an aliphatic alcohol (1–6C) are caused to react. This reaction is carried out at a temperature ranging from −20° C. to the boiling temperature of the reaction medium. As organic acid, there may be used trifluoroacetic acid optionally in an inert solvent such as a chlorine-containing solvent (for example dichloroethane) or formic acid (96%). As inorganic acid, there may be used concentrated aqueous hydrochloric acid or concentrated aqueous sulphuric acid.

In step c, an aliphatic alcohol (1–6C in a straight or branched chain) is caused to react in the presence of persulphuric acid. This reaction is generally carried out at a temperature of 10 to 15° C. The persulphuric acid can be obtained according to according to the method described by Nishihara, A. and Kubota, I. (J. Org. Chem., 33, 2525, (1968), procedure A).

In step d, the derivative (B) is hydrogenated. This hydrogenation is generally carried out in an inert organic solvent such as ethyl acetate or acetic acid or a mixture of the 2 solvents, by means of hydrogen, at a pressure of 1 to 2 bar, in the presence of palladized charcoal, at a temperature close to 20° C.

The derivative (A) of the preceding reaction scheme is new and forms part of the invention as well as the process for preparing it.

The compounds of formula (I) for which R represents an -alk-COOH radical in which alk is an alkyl radical containing 2 carbon atoms in a straight chain can also be prepared by hydrogenation of a corresponding compound of formula (I) for which R represents a —CH=CH—COOH radical.

This reaction can be carried out by any method which makes it possible to hydrogenate an acrylic derivative without affecting the rest of the molecule. In particular, this reaction is carried out by means of hydrogen, at a pressure of between 3 and 8 bar, in the presence of a hydrogenation catalyst such as palladized charcoal, in an aqueous sodium hydroxide solution, at a temperature of between 30 and 50° C.

The compounds of formula (I) for which R represents a phenyl radical substituted with a carboxyl radical can also be prepared by hydrolysis of a corresponding derivative for which the phenyl radical is substituted with a cyano radical.

This reaction is carried out preferably by means of an inorganic acid such as hydrochloric acid, in an aqueous medium, at the boiling temperature of the reaction medium.

The compounds of formula (I) can be purified by the usual known methods, for example by crystallization, chromatography or extraction.

The enantiomers of the compounds of formula (I) can be obtained by resolution of the racemates, for example by chromatography on a chiral column according to W. H. PIRCKLE et al., Asymmetric synthesis, vol. 1, Academic Press (1983) or by synthesis from chiral precursors.

The isomers and diastereoisomers of the compounds of formula (I) can be separated by the usual known methods, for example by crystallization or chromatography.

The compounds of formula (I) containing a basic residue can be optionally converted to addition salts with an inorganic or organic acid by the action of such an acid in an organic solvent such as an alcohol, a ketone, an ether or a chlorine-containing solvent.

The compounds of formula (I) containing an acidic residue can be optionally converted to metallic salts or to addition salts with nitrogen-containing bases according to methods known per se. These salts can be obtained by the action of a metallic (for example alkali metal or alkaline-earth metal) base, ammonia, an amine or a salt of an amine on a compound of formula (I), in a solvent. The salt formed is separated by the usual methods.

These salts also form part of the invention.

As examples of pharmaceutically acceptable salts, there may be mentioned the addition salts with inorganic or organic acids (such as acetate, propionate, succinate, benzoate, fumarate, maleate, oxalate, methanesulphonate, isethionate, theophyllinacetate, salicylate, methylene-bis-β-oxynaphthoate, chlorohydride, sulphate, nitrate and phosphate), the salts with alkali metals (sodium, potassium and lithium) or with alkaline-earth metals (calcium and magnesium), the salt of ammonium, the salts of nitrogen-containing bases (ethanolamine, trimethylamine, methylamine, benzylamine, N-benzyl-β-phenethylamine, choline, arginine, leucine, lysine, N-methylglucamine).

The compounds of formula (I) have useful pharmacological properties. These compounds are antagonists of the α-amino-3-hydroxy-5-methyl-4-isoxazolepropionic acid (AMPA) receptor, also known as quisqualate receptor.

Moreover, the compounds of formula (I) are non-competitive antagonists of the N-methyl-D-aspartate (NMDA) receptor and, more particularly, they are ligands for the glycine modulating sites of the NMDA receptor.

These compounds are therefore useful for treating or preventing all ischaemias (such as focal or global ischaemia) following cerebrovascular accidents such as thromboembolic and haemorrhagic stroke, a cardiac arrest, an arterial hypotension, a cardiac, vascular or pulmonary surgical operation or a severe hypoglycaemia. They are also useful in the treatment of effects due to anoxia, whether perinatal or following a drowning, a high pressure or cerebrospinal lesions. These compounds may also be used for treating or preventing the progression of neurodegenerative diseases, of HUNTINGTON's chorea, of ALZHEIMER's disease and other dementias, of amyotrophic lateral sclerosis or of other motor neurone diseases, of olivopontocerebellar atrophy and of PARKINSON's disease. These compounds can also be used against epileptogenic and/or convulsive manifestations, for the treatment of cerebral or spinal traumas, traumas linked to degeneration of the inner ear (R. PUJOL et al., Neuroreport, 3, 299–302 (1992) or of the retina (J. L. MONSINGER et al., Exp. Neurol., 113, 10–17 (1991), tinnitus, anxiety (KEHNE et al., Eur. J. Pharmacol., 193, 283 (1991)), depression (TRULLAS et al., Eur. J. Pharmacol., 185, 1 (1990)), schizophrenia (REYNOLDS, TIPS, 13, 116 (1992)), TOURETTE's syndrome, hepatic encephalopathies, sleep disorders, attention-deficit disorders, hormonal-condition disorders (excess secretion of GH or LX, secretion of corticosterone), as analgesics (DICKENSON et al., Neurosc. Letters, 121, 263 (1991)), anti-inflammatories (SLUTA et al., Neurosci. Letters, 149, 99–102 (1993)) antianoretics (SORRELS et al., Brain Res., 572, 265 (1992)), antimigraines, antiemetics and for treating poisoning by neurotoxins or other substances which are NMDA or AMPA receptor agonists, as well as neurological disorders associated with viral diseases such as viral meningitis and encephalitis, AIDS (LIPTON et al., Neuron, 7, 111 (1991)), rabies, measles and tetanus (BAGETTA et al., Br. J. Pharmacol., 101, 776 (1990)). These compounds are also useful for the prevention of, tolerance of and dependency on drug and alcohol withdrawal symptoms and inhibition of acquired tolerance of and dependency on opiates, barbiturates, amphetamines and benzodiazepines. They can also be used in the treatment of deficiencies linked to mitochondrial abnormalities such as mitochondrial myopathy, LEBER's syndrome, WERNICKE's encephalopathy, RETT's syndrome, homocysteinaemia, hyperprolinaemia, hydroxybutyric-aminoaciduria, saturnine encephalopathy (chronic lead poisoning) and sulphite oxidase deficiency.

The affinity of the compounds of formula (I) for the AMPA receptor was determined by studying the antagonism of the specific binding of [$^3$H]-AMPA to rat cerebral cortex membranes (HONORE et al., Neuroscience letters, 54, 27 (1985)). The [$^3$H]-AMPA is incubated in the presence of 0.2 mg of proteins at 4° C. for 30 minutes in 10 mM, $KH_2PO_4$, 100 mM KSCN, pH 7.5. Non-specific binding is determined in the presence of 1 mM L-glutamate. The bound radioactivity is separated by filtration on PH AAACIA filters (printed Filtermate A). The inhibitory activity of these products is less than or equal to 100 μM.

The affinity of the compounds of formula (I) for the glycine site linked to the NMDA receptor was determined by studying the antagonism of the specific binding of [$^3$H]-DCKA to rat cerebral cortex membranes according to the method described by T. CANTON et al., J. Pharm. Pharmacol., 44, 812 (1992). The [$^3$H]-DCKA (20 nM) is incubated in the presence of 0.1 mg of proteins at 4° C. for 30 minutes in 50 mM HEPES buffer, pH 7.5. Non-specific binding is determined in the presence of 1 mM glycine. The bound radioactivity is separated by filtration on Whatman GF/B filters. The inhibitory activity of these products is less than or equal to 100 μM.

The compounds of formula (I) have a low toxicity. Their LD50 is greater than 50 mg/kg by the IP route in mice.

The following examples illustrate the invention.

PREPARATION OF THE INTERMEDIATES OF FORMULA (IV)

EXAMPLE A ethyl 4-(diethoxyphosphoryl)imidazole-2-carboxylate

A solution of 1.2 g of ethyl (hydroxyamino)iminoacetate in 20 ml of chloroform and 1.4 ml of triethylamine is cooled to a temperature close to 10° C. and a solution of 1.54 g of diethyl ethynylphosphonate in 5 ml of chloroform is added dropwise. The reaction medium is stirred overnight at a temperature close to 20° C., supplemented with 0.15 g of diethyl ethynylphosponate and heated for 1 hour at a temperature close to 50° C. The reaction mixture is supplemented with 50 ml of dichloromethane and washed with 3×40 ml of saturated sodium chloride solution. The organic phase is evaporated in a rotary evaporator and the evaporation residue is supplemented with 40 ml of ethyl ether and filtered. The filtrate is evaporated in a rotary evaporator to give a yellow oil (2.4 g). 20 ml of xylene is added to this oil and the mixture is heated at reflux for 20 hours. The liquid phase is decanted off and evaporated in a rotary evaporator. The evaporation residue is purified by chromatography on a silica column, eluting with ethyl acetate. 0.5 g of ethyl 4-(diethoxyphosphoryl)imidazole-2-carboxylate is obtained in the form of a yellow oil [mass spectrum (electron impact) m/z 276 (M)$^+$, 247 (276-$C_2H_5$)$^+$, 231 (276-$C_2H_5O$)$^+$, 204 ($C_6H_9N_2O_4P$)$^+$, 157 ($C_4H_2N_2O_3P$)$^+$].

The ethyl (hydroxyamino)iminoacetate can be synthesized as described by W. K. WARBURTON, J. Chem. Soc. (C), 1522 (1966).

The diethyl ethynylphosphonate can be synthesized as described by D. T. MONAGHAN et al., Brain Res., 278, 138 (1983).

EXAMPLE B ethyl 4-(ethoxycarbonylmethyl)imidazole-2-carboxylate

A mixture of 2.5 g of ethyl (ethylthio)iminoacetate tetrafluoroborate, 110 ml of acetic acid, 1.8 g of ethyl 4-aminoacetoacetate hydrochloride and 1.64 g of sodium acetate is heated for 3 hours at a temperature close to 95° C. The reaction mixture is filtered and the insoluble matter is rinsed with 3×5 ml of acetic acid. The filtrate is evaporated in a rotary evaporator and the evaporation residue is supplemented with 75 ml of dichloromethane. The organic solution is dried over sodium sulphate, filtered and evaporated in a rotary evaporator. The evaporation residue (1.86 g) is purified by chromatography on a silica column, eluting with ethyl acetate. 1.5 g of ethyl 4-(ethoxycarbonylmethyl) imidazole-2-carboxylate are obtained in the form of a red-yellow solid melting at 88° C.

The ethyl (ethylthio)iminoacetate tetrafluoroborate can be synthesized as described by H. YAMANAKA et al., Chem. Pharm. Bull., 31(1), 4549 (1983).

The ethyl 4-aminoacetoacetate hydrochloride can be synthesized as described by D. E. ORR and A. J. MIAM, Chem. Ind. (London), 392 (1983).

EXAMPLE C diethyl 2-ethoxycarbonylimidazole-4-methylphosphonate

A solution of 2.85 g of triethyloxonium tetrafluoroborate in 10 ml of methylene chloride is added dropwise, at 20° C. over 15 minutes, to a solution of 1.33 g of ethyl thiooxamate in 50 ml of methylene chloride. After stirring for 16 hours at the same temperature, the solution is concentrated to dryness under reduced pressure. The product obtained is dissolved in 10 ml of acetic acid and there are added successively a solution of 2.7 g of diethyl glycylmethylphosphonate hydrochloride in 10 ml of acetic acid and 1.64 g of sodium acetate. The mixture is stirred for 3 hours at a temperature close to 95° C. and, after cooling to 20° C., the insoluble matter produced is separated by filtration and washed twice with a total of 30 ml of acetic acid. The filtrate and the washing are combined and concentrated to dryness under reduced pressure. The product obtained is chromatographed on a neutral silica gel, eluting with ethyl acetate and then with an ethyl acetate and methanol (90-10 by volume) mixture. The fractions containing the expected product are combined and concentrated to dryness under reduced pressure and 2 g of diethyl 2-ethoxycarbonylimidazole-4-methylphosphonate are thus obtained in the form of a red oil [$^1$H NMR spectrum in $CDCl_3$, T=300K, δ in ppm (250 MHz): 1.50 (6H, t, J=6 Hz, 2 $CH_3$), 1.60 (3H, t, J=6 Hz, $CH_3$), 3.50 (2H, d, J=20 Hz, $PCH_2$), 3.27 and 3.78 (1H each, m, $CH_2$), 3.90 (2H, s, $CH_2CO$), 4.30 (4H, q, J=6 Hz, $P(OCH_2—)_2$), 4.60 (2H, q, J=6 Hz, $OCH_2$), 7.40 (1H, s, imidazole CH), 12.0 (1H, s, NH)].

The diethyl glycylmethylphosphonate hydrochloride can be prepared in the following manner: 11 ml of an 8N hydrochloric dioxane solution is added dropwise, over 10 minutes, to a solution of 3.41 g of diethyl N-(t-butoxycarbonyl)glycylmethylphosphonate in 30 ml of dioxane. The mixture is stirred for 3 hours at the same temperature and then concentrated to dryness under reduced pressure at 40° C. The product obtained is suspended 3 times in a total of 225 ml of anhydrous ethyl ether and dried after removal of the supernatant solvent. 2.7 g of diethyl glycylmethylphosphonate hydrochloride are thus obtained in the form of a gummy product [$^1$H NMR spectrum in DMSO-$d_6$, T=300K, δ in ppm (250 MHz): 1.25 (6H, t, J=6 Hz, $CH_3$), 3.52 (2H, d, J=20 Hz, $PCH_2$), 4.00 (2H, s, $NCH_2CO$), 4.10 (4H, q, J=6 Hz, $P(OCH_2—)_2$), 8.55 (1H, s, $NH_2$)].

The diethyl N-(t-butoxycarbonyl) glycylmethylphosphonate can be prepared in the following manner: 8.1 g of 1,1'-carbonyldiimidazole are added, over 10 minutes at 20° C., to a solution of 8.75 g of N-(t-butoxycarbonyl)glycine in 200 ml of anhydrous tetrahydrofuran. The mixture is stirred for 2 hours at the same temperature and a solution A is thus obtained. 200 ml of a 1.6 M solution of n-butyllithium in hexane are added, over 45 minutes at –75° C. under an argon atmosphere, to a solution of 45.6 g of diethyl methylphosphonate in 400 ml of anhydrous tetrahydrofuran. The mixture is stirred for 75 minutes at the same temperature and a white suspension B is thus obtained. Solution A is then added dropwise, over 40 minutes under an argon atmosphere, to suspension B maintained at –75° C. The mixture is stirred for 1 hour at the same temperature and for 1 hour at –30° C., supplemented with 1.75 ml of acetic acid, poured over 1 l of a saturated aqueous sodium hydrogen carbonate solution and extracted 3 times with a total of 2100 ml of ethyl acetate. The organic extracts are combined, dried over anhydrous sodium sulphate, filtered and concentrated to dryness under reduced pressure at 40° C. The product obtained (23.6 g) is chromatographed on a neutral silica gel, eluting with ethyl acetate. The fractions containing the expected product are combined and concentrated to dryness under reduced pressure and 6.7 g of diethyl N-(t-butoxycarbonyl)glycylmethylphosphonate are thus obtained in the form of a colourless oil [$^1$H NMR spectrum in DMSO-$d_6$, T=300K, δ in ppm (200 MHz): 1.25 (6H, t, J=6 Hz, $CH_3$), 1.40 (9H, s, $C(CH_3)_3$), 3.27 (2H, d, J=20 Hz, $PCH_2$), 3.92 (2H, d, J=6 Hz, $NCH_2CO$), 4.10 (4H, q, J=6 Hz, $P(OCH_2—)_2$), 7.05 (1H, t, J=6 Hz, NH)].

EXAMPLE D ethyl 4(5)-(2-ethoxycarbonylethyl)-1H-imidazole-2-carboxylate

A solution of 4.2 g of ethyl (E)-4(5)-(2ethoxycarbonylvinyl)-1H-imidazole-2-carboxylate in 200 ml of ethyl acetate and 2 ml of acetic acid is hydrogenated in the presence of 1 g of 10% palladized charcoal for 2 hours at a temperature close to 20° C. and at a pressure close to 1.5 bar. The reaction mixture is filtered and evaporated in a rotary evaporator. 3.9 g of ethyl 4(5)-(2-ethoxycarbonylethyl)-1H-imidazole-2carboxylate are obtained in the form of a white solid melting at 87° C. [$^1$H NMR spectrum in $CDCl_3$, T=300K, δ in ppm (250 MHz): 1.16 (3H, t, J=6 Hz, $CH_3$), 1.30 (3H, t, J=6 Hz, $CH_3$), 2.65 (2H, t, J=6 Hz, $CH_2$), 2.81 (2H, t, J=6 Hz, $CH_2$), 4.06 (2H, q, J=6 Hz, $OCH_2$), 4.29 (2H, q, J=6 Hz, $OCH_2$), 7.02 (1H, s, imidazole CH)].

EXAMPLE E ethyl (E)-4(5)-(2-ethoxycarbonylvinyl)-1H-imidazole-2-carboxylate 260 g (0.05 mol) of persulphuric acid freshly prepared according to the method described by Nishihara, A. and Kubota, I. (J. Org. Chem., 33, 2525, (1968), procedure A) are added dropwise to a solution of 9.7 g of ethyl (E)-4(5)-(3-oxopropenyl)-1H-imidazole-2-carboxylate in 500 ml of ethanol, cooled to between 10 and 15° C. The stirring is continued for 1 hour and 30 minutes at this temperature. The reaction medium is then poured over ice, neutralized with a sodium carbonate solution and extracted with 2×750 ml of ethyl acetate. The organic phase is dried over magnesium sulphate and evaporated in a rotary evaporator. 8.2 g of ethyl (E)-4(5)-(2-ethoxycarbonylvinyl)-1H-imidazole-2-carboxylate are obtained in the form of a yellow solid melting at 161° C. [$^1$H NMR spectrum in $CDCl_3$+AcOH, T=300K, δ in ppm (250 MHz): 1.27 (3H, t, J=6 Hz, CH$_3$), 1.35 (3H, t, J=6 Hz, CH$_3$), 4.20 (2H, q, J=6 Hz, OCH$_2$), 4.39 (2H, q, J=6 Hz, OCH$_2$), 6.55 (1H, d, J=16 Hz, ethylenic CH), 7.40 (1H, s, imidazole CH), 7.55 (1H, d, J=16 Hz, ethylenic CH)].

EXAMPLE F ethyl (E)-4(5)-(3-oxopropenyl)-1H-imidazole-2-carboxylate

A solution of 80 g of (+/−)-(2,5-dihydro-2,5-dimethoxyfuran-2-ylmethyl)-(1-imino-2,2,2-trichloroethyl) amine in 80 ml of dichloromethane are added dropwise under an argon atmosphere to 80 ml of trifluoroacetic acid stirred and cooled to −15° C. The stirring is continued for 22 hours at a temperature close to 20° C. 250 ml of ethanol are then added and the mixture is heated at reflux. The dichloromethane is removed by distillation and then the heating at reflux is maintained for 3 hours and 30 minutes. After cooling, the reaction medium is neutralized with a solution of sodium hydrogen carbonate and extracted with 3×500 ml of ethyl acetate. The organic phase is dried over magnesium sulphate and evaporated in a rotary evaporator. The evaporation residue is purified by filtration on silica with ethyl acetate, and then trituration in diethyl ether. 9 g of ethyl (E)-4(5)-(3-oxopropenyl)-1H-imidazole-2-carboxylate are obtained in the form of a yellow solid melting at 151° C. [$^1$H NMR spectrum in DMSO, T=300K, δ in ppm (300 MHz): 1.35 (3H, t, J-6 Hz, CH$_3$), 4.39 (2H, q, J=6 Hz, OCH$_2$), 6.55 (1H, broad s, ethylenic CH), 7.45 (1H, d, J=16 Hz, ethylenic CH), 7.75 (1H, s, imidazole CH)].

The (+/−)-(2,5-dihydro-2,5-dimethoxyfuran-2-ylmethyl)-(1-imino-2,2,2-trichloroethyl)amine can be prepared in the following manner: 50 g of commercial (+/−)-2,5-dihydro-2,5-dimethoxyfurfurylamine are added dropwise under an argon atmosphere to a solution, stirred and cooled to a temperature close to −70° C., of 45.4 g of 2,2,2-trichloroacetonitrile in 80 ml of tetrahydrofuran. The stirring is continued for 2 hours at a temperature close to 20° C. The reaction medium is supplemented with 300 ml of ethyl acetate and washed with 2×100 ml of saline solution. The organic phase is dried over magnesium sulphate and evaporated in a rotary evaporator. 81.5 g of (+/−)-(2,5-dihydro-2, 5dimethoxyfuran-2-ylmethyl)-(1-imino-2,2,2-trichloroethyl)amine are obtained in the form of a viscous colourless oil [$^1$H NMR spectrum in CDCl$_3$, T=300K, δ in ppm (200 MHz): 50/50 mixture of the diastereoisomers: 3.05 and 3.10 (3H, B, CH$_3$), 3.35 (3H, s, CH$_3$), between 3.2 and 3.8 (2H, m, NCH$_2$), 5.35 and 5.65 (1H, s, OCH), between 5.70 and 6.10 (2H, m, 2 ethylenic CH), between 7.0 and 7.20 (1H, s, NH)].

EXAMPLE G ethyl 4(5)-(4-carbethoxyphenyl)-1H-imidazole-2-carboxylate

A solution of 2.85 g of triethyloxonium tetrafluoroborate in 10 ml of methylene chloride is added dropwise at 20° C. over 10 minutes to a solution of 1.33 g of ethyl thiooxamate in 50 ml of methylene chloride. The mixture is stirred for 16 hours at a temperature close to 20° C. and then concentrated to dryness under a reduced pressure (15 mm Hg; 2 kPa) at 40° C. The residue (3.4 g) is dissolved in 20 ml of acetic acid and 2.43 g of ethyl 4-glycylbenzoate hydrochloride and then 1.64 g of anhydrous sodium acetate are added. The mixture is stirred for 3 hours at 95° C. and then concentrated to dryness under reduced pressure (15 mm Hg; 2 kPa) at 60° C. The product obtained is supplemented with 50 ml of methylene chloride and with 50 ml of distilled water and, after decantation, the aqueous solution is extracted 3 times with a total of 90 ml of methylene chloride. The organic extracts are combined, dried over anhydrous sodium sulphate and concentrated to dryness under reduced pressure (15 mm Hg; 2 kPa) at 40° C. The residue is chromatographed on a neutral silica gel eluting with ethyl acetate. 2.1 g of ethyl 4(5)-(4-carbethoxyphenyl)-1H-imidazole-2-carboxylate melting at 174° C. are thus obtained.

The ethyl 4-glycylbenzoate hydrochloride can be prepared in the following manner: 11.2 ml of a 10 N aqueous hydrochloric acid solution are added to 120 ml of absolute ethanol. 8.8 g of ethyl 4-(N,N-diformylglycyl)benzoate are added to 84 ml of the solution thus obtained. The mixture is stirred for 16 hours at a temperature close to 20° C. and the insoluble matter produced is separated by filtration, washed 3 times with a total of 90 ml of ethyl ether and dried under reduced pressure. 4.1 g of ethyl 4-glycylbenzoate hydrochloride are thus obtained in the form of a white powder [$^1$H spectrum in DMSO-d$_6$, T=300K, δ in ppm (300 MHz): 1.30 (3H, t, J=6 Hz, CH$_3$), 4.35 (2H, q, J=6 Hz, OCH$_2$), 4.60 (2H, s, COCH$_2$N), 8.10 (4H, m, PhCO$_2$H), 8.70 (3H, 8, NH$_2$HCl)].

The ethyl 4-(N,N-diformylglycyl)benzoate can be prepared in the following manner: 5.2 g of sodium diformylamide are added to a solution of 13.55 g of ethyl 4-bromoacetylbenzoate in 125 ml of acetonitrile and the mixture is stirred for 3 hours 30 minutes at 80° C. and then for 16 hours at a temperature close to 20° C. The insoluble matter produced is removed by filtration and the filtrate is concentrated to dryness under reduced pressure (15 mm Hg; 2 kPa) at 40° C. The product obtained is suspended twice in a total of 150 ml of ethanol and, after filtration and drying (0.5 mm Hg; 0.07 kPa) at 40° C., 8.8 g of ethyl 4-(N,N-diformylglycyl)benzoate are obtained in the form of a beige solid melting at 105° C.

The ethyl 4-bromoacetylbenzoate can be prepared according to the method described in patent EP 44704.

EXAMPLE H ethyl 4(5)-(2-carbethoxyphenyl)-1H-imidazole-2-carboxylate

A solution of 5.7 g of triethyloxonium tetrafluoroborate in 25 ml of methylene chloride is added dropwise at 20° C. over 10 minutes to a solution of 2.66 g of ethyl thiooxamate in 100 ml of methylene chloride. The mixture is stirred for 16 hours at a temperature close to 20° C. and then concentrated to dryness under a reduced pressure (15 mm Hg; 2 kPa) at 40° C. The residue (6.4 g) is dissolved in 40 ml of acetic acid and 5.4 g of ethyl 2-glycylbenzoate hydrochloride and then 3.28 g of anhydrous sodium acetate are added. The mixture is stirred for 3 hours 30 minutes at 95° C., stored without stirring for 48 hours at a temperature close to 20° C. and then concentrated to dryness under reduced pressure (15 mm Hg; 2 kPa) at 40° C. The product obtained is supplemented with 150 ml of methylene chloride and the mixture is washed 3 times with a total of 150 ml of distilled water. The organic solution is dried over anhydrous sodium sulphate and concentrated to dryness under reduced pressure (15 mm Hg; 2 kPa) at 40° C. The product obtained is chromatographed on a neutral silica gel, eluting with ethyl acetate. 1.6 g of ethyl 4(5)-(2-carbethoxyphenyl)-1H-imidazole-2-carboxylate are thus obtained in the form of an orange-coloured oil [$^1$H spectrum in DMSO-d$_6$, T=300K, δ in ppm (300 MHz): 1.15 (3H, t, J=6 Hz, CH$_3$), 1.35 (3H, t, J=6 Hz, CH$_3$), 4.25 (2H, q, J=6 Hz, OCH$_2$), 4.40 (2H, q, J=6 Hz, OCH$_2$), 7.45 (1H, t, J=7 Hz, arom. CH), between 7.50 and 7.85 (4H, m, 3 arom. CH and imidazole CH), 13.60 (1H, s, NH)].

The ethyl 2-glycylbenzoate hydrochloride can be prepared in the following manner: 11.2 ml of a 10 N aqueous hydrochloric acid solution are added to 120 ml of absolute ethanol. 7 g of ethyl 2-(N,N-diformylglycyl)benzoate are added to 70 ml of the solution thus obtained. The mixture is stirred for 16 hours at a temperature close to 20° C. and concentrated to dryness under reduced pressure (15 mm Hg; 2 kPa) at 40° C. 5.46 g of ethyl 2-glycylbenzoate hydrochloride are thus obtained in the form of a brown gum used as is in the next step.

The 2-(N,N-diformylglycyl)benzonitrile can be prepared in the following manner: 5.54 g of sodium diformylamide are added to a solution of 14.45 g of ethyl 2-bromoacetylbenzoate in 150 ml of acetonitrile and the mixture is stirred for 16 hours at boiling temperature and then, after cooling to 20° C., the insoluble matter produced is removed by filtration and the filtrate is concentrated to dryness under reduced pressure (15 mm Hg; 2 kPa) at 40° C. The residue is chromatographed on a neutral silica gel, eluting with a methylene chloride-ethyl acetate (80-20 by volume) mixture. 8.4 g of ethyl 2-(N,N-diformylglycyl) benzoate are thus obtained in the form of an orange-coloured oil [$^1$H spectrum in DMSO-d$_6$, T=300K, δ in ppm (300 MHz): 1.22 (3H, t, J=6 Hz, CH$_3$), 4.23 (2H, q, J=6 Hz, OCH$_2$), 4.90 (2H, s, NCH$_2$CO), between 7.60 and 7.90 (4H, m, 4 arom. CH), 9.20 (2H, B, 2 CHO)].

The ethyl 2-bromoacetylbenzoate can be prepared according to the method described by VITI G. et al., J. Heterocyclic Chem., 28, 379 (1991).

PREPARATION OF THE COMPOUNDS OF FORMULA (I)

EXAMPLE 1

A mixture of 9.54 g of ethyl 1-[4-(1(2)-benzyltetrazol-5-ylmethyl)-1-oxoindan-2-yl]imidazole-carboxylate, 370 ml of acetic acid and 83 g of ammonium acetate are heated at reflux for 6 hours. The reaction mixture is evaporated in a rotary evaporator and the evaporation residue is treated with 400 ml of distilled water. The gummy precipitate produced is isolated and triturated with 150 ml of ethyl acetate. After filtration and washing with 50 ml of ethyl acetate, the solid is dried under vacuum (1 mm Hg; 0.13 kPa) at a temperature close to 60° C. 2.5 g of 9-(1(2)-benzyltetrazol-5-ylmethyl)-5H,10H-imidazo[1,2-a]indeno[1,2-e]pyrazin-4-one are obtained in the form of an off-white solid [$^1$H NMR spectrum in DMSO-d$_6$, T=300K (δ in ppm, 250 MHz): 75/25 mixture of the 2 isomers: predominant isomer: 4.0 (2H, CH$_2$), 4.4 (2H, s, CH$_2$), 5.9 (2H, CH$_2$Ph), between 7.2 and 7.5 (7H, 2 arom. and phenyl CH), 7.6 (1H, s, imidazole CH), 7.8 (1H, d, J=6 Hz, arom. CH), 8.0 (1H, s, imidazole CH), 12.4 (1H, s, NH); minor isomer: 3.95 (2H, CH$_2$), 4.5 (2H, s, CH$_2$), 5.8 (2H, CH$_2$Ph), between 6.9 and 7.5 (8H, arom. and phenyl CH), 7.6 (1H, s, imidazole CH), 7.95 (1H, s, imidazole CH), 12.4 (1H, s, NH)].

A mixture of 2 g of 9-(1(2)-benzyltetrazol-5-ylmethyl)-5H,10H-imidazo[1,2-a]indeno[1,2-e]pyrazin-4-one and 100 ml of hydrobromic acid at 47% in water is heated at a temperature close to 100° C. for 40 hours. The reaction mixture is filtered and the solid is washed several times with distilled water, and then with a mixture of 10 ml of methyl isobutyl ether and 20 ml of acetone and then with 2×40 ml of acetone. After air drying, the crude product (1.3 g) is treated, under ultrasound treatment, with 80 ml of 0.1 N sodium hydroxide and the brown solution obtained is washed with 40 ml of ethyl acetate, stirred with a little vegetable charcoal, filtered and acidified to pH 1 with 1 N hydrochloric acid. The suspension obtained is filtered and the solid is washed with 2×20 ml of distilled water, and then 4×15 ml of acetone and 3×15 ml of methyl isobutyl ether. After drying under vacuum (1 mm Hg; 0.13 kPa) at a temperature close to 60° C., 0.8 g of 9-(1-tetrazol-5-ylmethyl))-5H,10H-imidazo[1,2-a]indeno[1,2-e]pyrazin-4-one is obtained in the form of a partly salified grey solid melting above 260° C. [Analysis: C$_{15}$H$_{11}$N$_7$O, 0.33 HCl; % calculated C: 56.75, H: 3.60, Cl: 3.72, N: 30.89, O: 5.04, % found C: 57.1, H: 3.2, Cl: 4.0, N: 30.8].

The ethyl 1-[4-(1(2)-benzyltetrazol-5ylmethyl)-1-oxoindan-2-yl]imidazole-2-carboxylate can be prepared in the following manner: a mixture of 0.7 g of 4-(1(2)-benzyltetrazol-5-ylmethyl)-2-bromoindan-1-one, 20 ml of acetone and 3.33 g of potassium carbonate is heated to the reflux temperature under an argon atmosphere. A solution of 1.92 g of ethyl imidazole-2-carboxylate in 20 ml of acetone is then added and the refluxing is continued for 2 hours. The reaction mixture is filtered and the filtrate is evaporated in a rotary evaporator. 2.07 g of ethyl 1-[4-(1(2)-benzyltetrazol-5-ylmethyl)-1-oxoindan-2-yl]imidazole-2-carboxylate are obtained in the form of a greenish black foam used as is in the subsequent syntheses.

The ethyl imidazole-2-carboxylate can be obtained as described in U.S. Pat. No. 3,600,399.

The 4-(1(2)-benzyltetrazol-2-ylmethyl)-2bromoindan-1-one can be prepared in the following manner: a solution of 1.65 ml of bromine in 10 ml of dichloromethane is added dropwise to a solution, stirred and cooled to a temperature close to 5° C., of 9.8 g of 4-(1(2)-benzyltetrazol-5-ylmethyl) indan-1-one in 100 ml of dichloromethane, under an argon atmosphere, and the stirring is continued for two hours at a temperature close to 20° C. The reaction mixture is washed with 4×100 ml of saline solution and the organic phase is dried over magnesium sulphate, filtered and the filtrate is evaporated in a rotary evaporator. 12.1 g of 4-(1(2)-benzyltetrazol-5-ylmethyl)-2-bromoindan-1one are obtained in the form of a brown oil used as is in the subsequent syntheses.

The 4-(1(2)-benzyltetrazol-5-ylmethyl)-indan-1-one can be prepared in the following manner: a mixture of 6.89 g of 4-(1H-tetrazol-5-ylmethyl)-indan-1-one, 150 ml of acetone, 4.3 g of potassium carbonate and 4 ml of benzyl bromide is heated at reflux for 4 hours under an argon atmosphere. The reaction mixture is filtered while still hot, the insoluble matter is rinsed with 3×30 ml of acetone and the filtrate is evaporated in a rotary evaporator. 9.8 g of 4-(1(2)-benzyltetrazol-5-ylmethyl)-indan-1-one are obtained in the form of a yellow oil [mass spectrum (electron impact) m/z 350 (M)$^+$, 213 (350-C$_7$H$_7$)$^+$, 158 (C$_8$H$_6$N$_4$)$^+$, 145 (C$_{10}$H$_9$O)$^+$, 91 (C$_7$H$_7$)$^+$].

The 4-(1H-tetrazol-5-ylmethyl)indan-1-one can be prepared in the following manner: 9.29 g of 3-[2(1H-tetrazol-5-ylmethyl)phenyl]propionic acid are added all at once under an argon atmosphere to 50 ml of concentrated sulphuric acid heated to a temperature close to 100° C. The heating is continued for 50 minutes at a temperature close to 110° C. The reaction mixture is poured over 300 g of crushed ice and stirred for two hours. The beige suspension obtained is filtered and the solid is washed with 3×20 ml of distilled water and dried under vacuum (1 nm Hg; 0.13 kPa) at a temperature close to 60° C. 5.5 g of 4-(1H-tetrazol-5-ylmethyl)indan-1-one are obtained in the form of a light beige solid melting at 222° C. [$^1$H NMR spectrum in DMSO-d$_6$, T=300K (δ in ppm, 300 MHZ): 2.65 (2H, m, COCH$_2$), 3.05 (2H, m, CH$_2$), 4.40 (2H, s, CH$_2$), 7.45 (1H, t, J=6 Hz, arom. CH), 7.60 (2H, m, 2 arom. CH)].

The 3-[2-(1H-tetrazol-5-ylmethyl)phenyl]propionic acid can be prepared in the following manner: a solution of 3.2 g of 3-[2-(1(2)-benzyltetrazol-5-ylmethyl)phenyl]acrylic acid in 50 ml of 0.5 N sodium hydroxide is hydrogenated for 21 hours at a temperature close to 20° C. at a pressure close to 1.5 bar, in the presence of 0.3 g of 10% palladized charcoal. The reaction mixture is filtered and then the filtrate is acidified to pH 1 with 1 N hydrochloric acid and extracted with 3×50 ml of ethyl acetate. The organic phase is washed with 30 ml of distilled water, dried over magnesium sulphate, filtered and evaporated in a rotary evaporator. 2.16 g of 3-[2-(1H-tetrazol-5ylmethyl)phenyl]propionic acid are obtained in the form of a white solid melting at 160° C.

The 3-[2-(1(2)-benzyltetrazol-5-ylmethyl)phenyl]acrylic acid can be prepared in the following manner: a mixture of 117.5 g of 1(2)-benzyl5-(2-bromobenzyl)tetrazole, 162 ml of tributylamine, 4.14 g of tri(o-tolyl)phosphine, 0.76 g of palladium acetate and 29.2 of acrylic acid is heated for 16 hours under an argon atmosphere at a temperature close to 100° C. The reaction medium is poured over a stirred mixture of 700 ml of 1 N hydrochloric acid and 1400 ml of ethyl acetate. The organic phase is washed with 2×400 ml of distilled water and then with 2×750 ml of water containing 20 g of sodium carbonate. The aqueous phases are combined, acidified to pH 1 with 6 N hydrochloric acid and extracted with 2×500 ml of ethyl acetate. The organic extract is washed with 250 ml of distilled water, dried over magnesium sulphate, filtered and evaporated in a rotary evaporator. 77.8 g of 3-[2-(1(2)-benzyltetrazol-5-ylmethyl)phenyl]acrylic acid are obtained in the form of a cream-coloured solid used as is in the subsequent syntheses.

The 1(2)-benzyl-5-(2-bromobenzyl)tetrazole can be prepared in the following manner: a mixture of 81.5 g of 5-(2-bromobenzyl)tetrazole, 800 ml of acetone, 45.4 g of potassium carbonate and 44.6 ml of benzyl bromide is heated at reflux for 5 hours under an argon atmosphere. The reaction mixture is filtered and the solid is rinsed with 2×100 ml of acetone and then the filtrate is evaporated in a rotary evaporator. 117.5 g of 1(2)benzyl-5-(2-bromobenzyl) tetrazole are obtained in the form of an orange-coloured liquid used as is in the subsequent syntheses.

The 5-(2-bromobenzyl)tetrazole can be prepared in the following manner: a mixture of 80 g of (2-bromophenyl) acetonitrile, 160 ml of dimethylformamide, 29.2 g of sodium azide and 24 g of ammonium chloride is heated for 3 hours at a temperature close to 100° C., and then at reflux for 3 hours, under an argon atmosphere. After stopping the heating, 29.2 g of sodium azide and 24 g of ammonium chloride are added and the mixture is again heated for 16 hours at a temperature close to 100° C. The reaction mixture is poured over 2 litres of a mixture of water and ice, acidified to pH 4–5 with 60 ml of acetic acid and stirred for 2 hours at a temperature close to 20° C. The cream-coloured suspension obtained is filtered and the solid is washed with 150 ml of distilled water, stirred with 2 litres of water containing 45 g of sodium carbonate and extracted with 2×250 ml of methyl tert-butyl ether. The aqueous phase is filtered and acidified to pH 1 with 6 N hydrochloric acid. The white suspension obtained is filtered and the solid is washed with 200 ml of distilled water and dried under vacuum (1 mm Hg; 0.13 kPa) at close to 60° C. 81.5 g of (2-bromobenzyl)tetrazole are obtained in the form of a white solid melting at 139° C.

EXAMPLE 2

A mixture of 11.2 g of diethyl 1-[4-(1(2)benzyltetrazol-5-ylmethyl)-1-oxoindan-2-yl]imidazole-2,4-dicarboxylate, 400 ml of acetic acid and 87.5 g of ammonium acetate are heated at reflux for 4 hours. The reaction mixture is concentrated in a rotary evaporator and the residue is stirred for 15 minutes with 750 ml of distilled water. The brown suspension obtained is filtered and the solid is washed successively with 2×125 ml of distilled water and 4×100 ml of ethyl acetate. After air drying, 3.87 g of ethyl 9-(1(2)-benzyltetrazol-5-ylmethyl)-4,5-dihydro-4-oxo-10H-imidazo[1,2-a]indeno[1,2-e]pyrazine-2-carboxylate are obtained in the form of brown solid [$^1$H NMR spectrum in DMSO-d$_6$, T=300K (δ in ppm, 250 MHz): 60/40 mixture of the 2 isomers: predominant isomer: 1.4 (3H, CH$_3$), 4.0 (2H, CH$_2$), between 4.3 and 4.6 (4H, CH$_2$ and OCH$_2$), 5.9 (2H, CH$_2$Ph), between 7.2 and 7.9 (5H, phenyl CH), 8.5 (1H, s, imidazole CH), 12.5 (1H, s, NH); minor isomer: 1.4 (3H, CH$_3$), 3.9 (2H, CH$_2$), between 4.3 and 4.6 (4H, CH$_2$ and OCH$_2$), 5.8 (2H, CH$_2$Ph), between 7.0 and 7.6 (5H, phenyl CH), 8.5 (1H, s, imidazole CH), 12.5 (1H, s, NH)].

A mixture of 3 g of ethyl 9-(1(2)-benzyltetrazol-5-ylmethyl)-4,5-dihydro-4-oxo-10H-imidazo[1,2-a]indeno[1, 2-e]pyrazine-2-carboxylate and 150 ml of hydrobromic acid at 47% in water is heated for 20 hours at a temperature close to 100° C. The is reaction mixture is filtered and the solid is washed with 4×50 ml of distilled water, and then with 4×50 ml of acetone and finally 2×50 ml of methyl tert-butyl ether. The solid is then stirred, in the presence of ultrasound, with 65 ml of 0.1 N sodium hydroxide and 20 the aqueous phase is washed with 30 ml of ethyl acetate, supplemented with 0.13 g of vegetable charcoal and filtered. The filtrate is acidified to pH 1 with 1 N hydrochloric acid and the precipitate formed is filtered and dried under vacuum (1 mm Hg; 0.13 kPa) at close to 60° C. 0.94 g of 9-(1H-tetrazol-5-ylmethyl))-4,5-dihydro-4-oxo-10H-imidazo[1,2-a]indeno [1,2-e]pyrazine-2-carboxylic acid is obtained in the form of a pale pink solid melting above 260° C. [Analysis: C$_{16}$H$_{11}$N$_7$O$_3$, % calculated C: 55.02, H: 3.17, N: 28.07, O: 13.74, % found C: 55.3, H: 2.8, N: 27.9].

The diethyl 1-[4-(1(2)-benzyltetrazol-5-ylmethyl)-1-oxoindan-2-yl]imidazole-2,4-dicarboxylate can be prepared in the following manner: a mixture of 5.3 g of diethyl imidazole-2,4-dicarboxylate, 100 ml of acetone and 16.7 g of potassium carbonate is heated to reflux temperature under an argon atmosphere. A solution of 9.58 g of 4-(1(2)-benzyltetrazol-5-yl)methyl-2-bromoindan-1-one in 50 ml of acetone is then added and the refluxing is continued for 4 hours. The reaction mixture is filtered, the insoluble matter is washed with 3×100 ml of acetone and the organic phase is evaporated in a rotary evaporator. 11.2 g of diethyl 1-[4-(1(2)-benzyltetrazol-5-ylmethyl)-1oxoindan-2-yl] imidazole-2,4-carboxylate are obtained in the form of a black foam used as is in the subsequent syntheses.

The diethyl imidazole-2,4-dicarboxylate can be synthesized as described by P. S. BRANCO et al., Tetrahedron, 48(30), 6335 (1992).

EXAMPLE 3

A mixture of 3.8 g of ethyl 1-[4-(1(2)-benzyltetrazol-5-ylmethyl)-1-oxoindan-2-yl]-4-(diethoxyphosphoryl) imidazole-2-carboxylate, 33 ml of acetic acid, 21 ml of a 5

N ammoniacal solution in methanol and 5 g of ammonium acetate is heated at reflux for 38 hours. The reaction mixture is concentrated in a rotary evaporator and the residue is supplemented with 100 ml of distilled water and extracted with 2×50 ml of ethyl acetate. The organic phase is dried over magnesium sulphate, filtered and evaporated in a rotary evaporator. The evaporation residue is stirred overnight with 80 ml of methyl tert-butyl ether and 8 ml of ethyl acetate at a temperature close to 20° C. and filtered. After air drying, 1.5 g of diethyl 9-(1(2)-benzyltetrazol-5-ylmethyl)-4,5-dihydro-4-oxo-10H-imidazo[1,2-a]indeno[1,2-e]pyrazine phosphonate are obtained in the form of a light beige solid [$^1$H NMR spectrum in DMSO-$d_6$, T=300K (δ in ppm, 300 MHz): 70/30 mixture of the 2 isomers: predominant isomer: 1.3 (6H, t, J=6 Hz, 2 $CH_3$), 4.0 (2H, s, $CH_2$), 4.15 (4H, m, $OCH_2$), 4.4 (2H, s, $CH_2$), 5.9 (2H, s, $CH_2$), between 7.2 and 7.6 (7H, m, arom. and phenyl CH) 7.8 (1H, d, J=6 Hz, arom. CH), 8.45 (1H, s, imidazole CH), 12.5 (1H, s, NH); minor isomer: 1.3 (6H, t, J=6 Hz, 2 $CH_3$), 3.95 (2H, s, $CH_2$), 4.15 (4H, m, $OCH_2$), 4.5 (2H, s, $CH_2$), 5.8 (2H, s, $CH_2$), between 7.0 and 7.6 (8H, m, arom. and phenyl CH), 8.45 (1H, s, imidazole CH), 12.5 (1H, s, NH)].

A mixture of 1.15 g of diethyl 9-(1(2)-benzyltetrazol-5-ylmethyl)-4,5-dihydro-4-oxo-10H-imidazo[1,2-a]indeno[1,2-e]pyrazine-2-phosphonate and 60 ml of hydrobromic acid at 47% in water is heated at a temperature close to 110° C. for 2 hours, and then at 100° C. for 16 hours, under an argon atmosphere. The reaction mixture is filtered and the solid is washed with 4×10 ml of distilled water, and then with 3×40 ml of methyl tert-butyl ether. After drying under vacuum (1 mm Hg; 0.13 kPa) at close to 60° C., 0.43 g of 9-(1H-tetrazol-5-ylmethyl))-4,5-dihydro-4-oxo10H-imidazo[1,2-a]indeno[1,2-e]pyrazine-2-phosphonic acid is obtained in the form of a pink solid melting above 260° C. [Analysis: $C_{15}H_{12}N_7O_4P$, % calculated C: 46.76, H: 3.14, N: 25.45, O: 16.61, P: 8.04, % found C: 46.7, H: 2.8, N: 25.1].

Ethyl 1-[4-(1(2)-benzyltetrazol-5-ylmethyl)-1-oxoindan-2-yl]-4-(diethoxyphosphoryl)imidazole-2-carboxylate can be prepared in the following manner: the procedure is carried out as in Example 2 for the preparation of diethyl 1-[4-(1(2)-benzyltetrazol-5-ylmethyl)-1-oxoindan-2-yl]imidazole-2,4-dicarboxylate, but starting with 2.76 g of ethyl 4-(diethoxyphosphoryl)imidazole-2-carboxylate, 100 ml of acetone, 6.7 g of potassium carbonate and 3.83 g of 4-(1(2)-benzyltetrazol-5-ylmethyl)-2-bromoindan-1-one. The crude product (5.7 g) is purified by chromatography on a silica column, eluting with a mixture of dichloromethane and methanol (95-5 by volume). 3.8 g of ethyl 1-[4-(1(2)-benzyltetrazol-5-ylmethyl)-1-oxoindan-2-yl]-4-(diethoxyphosphoryl)imidazole-2-carboxylate are obtained in the form of a brown foam used as is in the subsequent syntheses.

EXAMPLE 4

A mixture of 1.63 g of ethyl 1-[4-(ethoxycarbonylmethyl)-1-oxoindan-2-yl]-4-(ethoxycarbonylmethyl)imidazole-2-carboxylate, 15 ml of acetic acid and 2.83 g of ammonium acetate is heated at reflux for 5 hours. The heating is stopped, 1.4 g of ammonium acetate are added and the refluxing is continued for 2 hours. The reaction mixture is poured over 100 ml of crushed ice and extracted with 3×50 ml of dichloromethane. The organic phase is dried over magnesium sulphate, filtered and evaporated in a rotary evaporator. The evaporation residue is suspended in 15 ml of ethyl acetate to give 0.8 g of diethyl 4,5-dihydro-4-oxo-10H-imidazo[1,2-a]indeno[1,2-e]pyrazine-2,9-diacetate in the form of a beige solid [$^1$H NMR spectrum in DMSO-$d_6$, T=300K, δ in ppm, (250 MHz): 1.25 (6H, m, 2 $CH_3$), 3.80 (4H, s, 2 $CH_2CO_2Et$), 4.00 (2H, s, $CH_2$), 4.15 (4H, q, J=6 Hz 2 $OCH_2$), 7.15 (1H, d, J=8 Hz, arom. CH), 7.40 (1H, t, J=8 Hz, arom. CH), 7.80 (1H, d, J=8 Hz, arom. CH), 7.90 (1H, s, arom. CH), 12.4 (1H, s, CONH)].

A mixture of 0.68 g of diethyl 4,5-dihydro-4-oxo-10H-imidazo[1,2-a]indeno[1,2-e]pyrazine-2,9-diacetate and 20 ml of 6 N hydrochloric acid is heated for 16 hours at a temperature close to 100° C. The reaction mixture is cooled on a water and ice bath and the suspension is filtered. The insoluble matter is washed with 3×10 ml of acetone and dried under vacuum (1 mm Hg; 0.13 kPa) at close to 60° C. 0.43 g of 4,5dihydro-4-oxo-10H-imidazo[1,2-a]indeno[1,2-e]pyrazine-2,9-diacetic acid hydrochloride is obtained in the form of a dark beige solid melting above 250° C. [Analysis: $C_{17}H_{13}N_3O_5$, HCl, % calculated C: 54.34, H: 3.76, Cl: 9.43, N: 11.18, O: 21.29, % found C: 53.9, H: 3.4, Cl: 9.8, N: 10.9, O: 20.9].

The ethyl 1-[4-(ethoxycarbonylmethyl)-1oxoindan-2-yl]-4-(ethoxycarbonylmethyl)imidazole-2 carboxylate, can be prepared in the following manner: a mixture of 1.37 g of ethyl 4-(ethoxycarbonylmethyl)imidazole-2-carboxylate, 30 ml of acetone and 4.14 g of potassium carbonate is heated to the reflux temperature. A solution of 1.78 g of ethyl (2-bromo-1-oxoindan-4-yl)acetate in 10 ml of acetone is then added over 10 minutes and the refluxing is continued for 3 hours. The reaction mixture is filtered while still hot and the filtrate is evaporated in a rotary evaporator. The evaporation residue is purified by chromatography on a silica column, eluting with ethyl acetate. 1.65 g of ethyl 1-[4-(ethoxycarbonylmethyl)-1-oxoindan-2-yl]-4-(ethoxycarbonylmethyl)imidazole-2-carboxylate, are obtained in the form of a brown oil [$^1$H NMR spectrum in DMSO-$d_6$, T=300K, δ in ppm (300 MHz): 1.20 (9H, m, 3 $CH_3$), 3.25 (1H, dd, J=5 and 14 Hz, HCH), 3.70 (2H, s, $CH_2CO$), 3.75 (1H, dd, J=7 and 14 Hz, HCH), 3.85 (2H, s, $CH_2CO$), 4.10 (6H, m, 3 $OCH_2$), 5.80 (1H, dd, J=5 and 7 Hz, CH), 7.50 (2H, m, 2 arom. CH), 7.70 (2H, d, J=8 Hz, 2 arom. CH)].

The ethyl (2-bromo-1-oxoindan-4-yl)acetate can be prepared in the following manner: 2.15 ml of a bromine solution in 20 ml of dichloromethane are added, over 10 minutes, to 10.45 g of ethyl ester of (1-oxoindan-4-yl)acetic acid in 130 ml of dichloromethane, at a temperature close to 5° C. and under an argon atmosphere. The reaction medium is allowed to return to a temperature close to 20° C. and the reaction is continued for 2 hours. The reaction mixture is poured into 100 ml of water saturated with sodium chloride. The organic phase is washed with twice 100 ml of distilled water before being dried and concentrated to give 12.7 g of expected product in the form of a brown oil used as is in the subsequent syntheses.

The ethyl ester of (1-oxoindan-4-yl)acetic acid can be prepared in the following manner: 4.7 ml of oxalyl chloride are added to 9.4 g of (1-oxoindan-4-yl)acetic acid in 200 ml of dichloromethane, at room temperature and under an argon atmosphere. After stirring for 4 hours at a temperature close to 20° C., 40 ml of ethanol are added to the reaction medium and the stirring is continued for 1 hour. The organic phase is washed with twice 25 ml of a saturated sodium hydrogen carbonate solution and then with twice 100 ml of distilled water and then dried and concentrated to give 10.45 g of expected product in the form of a brown oil used as is in the subsequent syntheses.

The (1-oxoindan-4-yl)acetic acid can be prepared in the following manner: 43 g of 3-(2-carboxymethylphenyl)

propionic acid in 250 ml of sulphuric acid (95%) are heated at 100° C. for 18 hours. After cooling to a temperature close to 20° C., the reaction medium is poured over 1000 ml of ice-cold water. The medium is extracted with three times 400 ml of ethyl acetate and the organic phase is washed with water, dried and concentrated to give 9.56 g of an orange-coloured solid. The product thus obtained is suspended in 50 ml of petroleum ether, filtered and then washed with 25 ml of isopropyl ether, dried under reduced pressure (1 mm Hg; 0.13 kPa) at 60° C. to give 6.7 g of an orange-yellow solid melting at 160° C.

The 3-(2-carboxymethylphenyl)propionic acid can be prepared in the following manner: 39.6 g of 3-(2-carboxymethylphenyl)acrylic acid with 3 g of 10% palladized charcoal in 400 ml of acetic acid are hydrogenated at a temperature close to 20° C. at a pressure of 1.2 bar for 4 hours. After filtration of the reaction medium, the organic phase is concentrated under reduced pressure (15 mm Hg; 2 kPa) at 40° C. The white solid obtained is suspended in 100 ml of petroleum ether and then filtered and dried under reduced pressure (1 mm Hg; 0.13 kPa) at 20° C. to give 39.3 g of a white solid melting at 138° C.

The 3-(2-carboxymethylphenyl)acrylic acid can be prepared in the following manner: 63.8 g of 2bromophenylacetic acid, 25.5 ml of acrylic acid, 3.6 g of tri(2-tolyl) phosphine, 0.67 g of palladium acetate in 211 ml of tributylamine are heated at 100° C. for 6 hours. After cooling to a temperature close to 20° C., the reaction medium is poured over 420 ml of water and 80 ml of concentrated hydrochloric acid. The medium is extracted with 3 times 500 ml of ethyl acetate; the organic phase is filtered, washed with 3 times 500 ml of water and then stirred in the presence of 800 ml of water and 35 g of sodium carbonate at a temperature close to 20° C. for 15 minutes. The aqueous phase is then acidified with 700 ml of 1 N hydrochloric acid. The precipitate formed is filtered, washed with water and then dried under reduced pressure (1 mm Hg; 0.13 kPa) at 60° C. to give 39.6 g of a white solid melting at 190° C.

EXAMPLE 5

A mixture of 3.13 g of ethyl 1-(4-cyanomethyl-1-oxoindan-2-yl)imidazole-2-carboxylate, 30 ml of acetic acid and 20 ml of 5 N ammoniacal methanol is heated at reflux for 20 hours. After cooling to a temperature close to 20° C., the reaction medium is concentrated and the residue thus obtained is taken up in 150 ml of water. The precipitate thus formed is filtered on sintered glass, rinsed with water and then dried under reduced pressure at 20° C. 2.6 g of a chestnut-coloured solid are thus obtained. This solid is taken up, with stirring, in 30 ml of a dichloromethane-methanol (95/5 by volume) mixture, filtered on sintered glass, rinsed with 2×30 ml of the same mixture and then dried under reduced pressure at 60° C. 0.84 g of 9-cyanomethyl-5H, 10H-imidazo[1,2-alindeno[1,2-e]pyrazin-4-one in the form of a beige solid melting above 260° C. is thus obtained [Analysis: $C_{15}H_{10}N_4O$, 0.2 $H_2O$, 0.17 $CH_3COOH$, % calculated C: 68.70, H: 3.84, N: 21.36, O: 6.10, % found C: 69.1, H: 3.5, N: 20.8].

The ethyl 1-(4-cyanomethyl-1-oxoindan-2yl)imidazole-2-carboxylate can be obtained in the following manner: a solution of 1.8 g of ethyl imidazole-2-carboxylate in 30 ml of acetone is supplemented with 8.6 g of potassium carbonate. This suspension is heated at reflux for 15 minutes and then a solution of 3.22 g of 2-bromo-4-(cyanomethyl)indan-1-one in 30 ml of acetone is added. After stirring for 4 hours at reflux temperature, the reaction medium is brought to a temperature close to 20° C. and filtered on sintered glass. The filtrate is evaporated and 2.7 g of a black solid are obtained. The purification by flash chromatography on a silica column (eluent: dichloromethane-ethyl acetate (50-50 by volume)) of this solid gives 0.62 g of ethyl 1-(4-cyanomethyl-1-oxoindan-2-yl)imidazole-2-carboxylate in the form of a brown solid [mass spectrum m/z 309 ($M^+$), 236 ((M-$CO_2$Et), $^+$), 141 (($C_6H_9N_2)^+$), 68(($C_3H_4)^+$)].

The ethyl imidazole-2-carboxylate can be prepared as described in U.S. Pat. No. 3,600,399.

The 2-bromo-4-(cyanomethyl)indan-1-one can be synthesized in the following manner: a solution of 0.72 ml of bromine in 5 ml of dichloromethane is added dropwise at 5° C. to a solution of 2.42 g of 4-(cyanomethyl)indan-1-one in 25 ml of dichloromethane. After 3 hours at a temperature close to 22° C., the reaction medium is taken up in 30 ml of salt water, stirred and then decanted. The organic phase is washed with 3×30 ml of salt water, dried over magnesium sulphate and evaporated. 3.22 g of 2-bromo-4-(cyanomethyl)indan-1-one are thus obtained in the form of a beige solid [Rf=0.36; thin-layer chromatography on silica gel, eluent: cyclohexane-ethyl acetate (2/1 by volume)].

The 4-(cyanomethyl)indan-1-one can be prepared in the following manner: 3.78 g of 3-(2-cyanomethylphenyl) propanoic acid are added to a solution of 3 ml of thionyl chloride and 15 ml of dichloromethane. After 0.55 ml of dimethylformamide is added, the reaction medium is heated at 30° C. for 4 hours. Evaporation of the medium leads to an orange-coloured oil. This oil is solubilized in 25 ml of 1,2-dichloroethane, and is then added dropwise at 10° C. under an argon atmosphere to a solution of 8 g of aluminium chloride and 35 ml of 1,2-dichloroethane. After 18 hours of reaction at a temperature close to 20° C., the reaction medium is poured over 60 g of ice. The solution is then decanted and the aqueous phase is extracted with 50 ml of dichloromethane. The combined organic phases are washed with 100 ml of a saturated aqueous sodium bicarbonate solution, with 50 ml of water and then dried over magnesium sulphate and evaporated. The solid residue thus obtained is triturated in 50 ml of methyl tert-butyl ether and the suspension obtained is filtered on sintered glass, rinsed with 25 ml of methyl tert-butyl ether and dried under reduced pressure at 20° C. 2.42 g of 4-(cyanomethyl)indan-1-one are thus obtained in the form of a beige solid ($^1$H NMR spectrum in DMSO-$d_6$, T=300K, δ in ppm (300 MHz); 2.70 (2H, m, $CH_2$), 3.15 (2H, m, $CH_2$), 4.20 (2H, s, $CH_2CN$), 7.52 (1H, t, J=8 Hz, arom. CH), 7.67 (1H, d, J=8 Hz, arom. CH), 7.73 (2H, d, J=8 Hz, arom. CH)].

The 3-(2-cyanomethylphenyl)propanoic acid can be prepared in the following manner: 1.5 g of 10% palladium on charcoal are added to a solution of 15.4 g of 3-(2-cyanomethyl)cinnamic acid in 250 ml of water and 83 ml of 1 N sodium hydroxide. This solution is placed under hydrogen at a pressure close to 1.5 bar and at a temperature close to 20° C. for 2 hours and 45 minutes. The reaction medium is then filtered on paper. The filtrate is acidified to pH close to 1 by addition of 80 ml of aqueous hydrochloric acid (1 N). The precipitate thus obtained is filtered on sintered glass, washed with 2×75 ml of water and dried under reduced pressure at a temperature close to 60° C. 13.46 g of 3-(2-cyanomethylphenyl)propanoic acid are thus obtained in the form of a white solid used as is in the subsequent syntheses.

The 3-(2-cyanomethyl)cinnamic acid can be obtained in the following manner: 13 ml of 2-bromophenylacetonitrile, 47.5 ml of tributylamine, 1.2 g of tri-o-tolylphosphine, 0.22 g of palladium acetate, and then 8.6 ml of acrylic acid are introduced successively into a round-bottomed flask under a nitrogen atmosphere. The mixture is heated for 18 hours at 100° C. After returning to a temperature close to 20° C., the reaction medium is taken up in 150 ml of ethyl acetate and 220 ml of 1 N aqueous hydrochloric acid. After stirring, the reaction medium is decanted and the aqueous phase is extracted with 150 ml of ethyl acetate. The organic phases are combined, washed with 2×200 ml of water, filtered and taken up in a solution of 10.6 g of sodium bicarbonate in 300 ml of water. After stirring for one hour and decantation, the aqueous phase is acidified with 17.5 ml of aqueous hydrochloric acid (12 N). The precipitate thus obtained is filtered on sintered glass, washed with 2×100 ml of water and dried under reduced pressure at a temperature close to 20° C. 15.4 g of 3-(2-cyanomethyl)cinnamic acid are thus obtained in the form of a white solid used as is in the subsequent syntheses.

EXAMPLE 6

A solution of 2.15 g of diethyl 1-(4-ethoxycarbonylmethyl-1-oxoindan-2-yl)-2-ethoxycarbonylimidazole-4-methylphosphonate and 3.23 g of ammonium acetate in 20 ml of acetic acid is stirred at boiling temperature for 2 hours and then for 7 hours after a further addition of 1.4 g of ammonium acetate. The mixture is cooled to a temperature close to 20° C. and the solid is separated by filtration, washed twice with a total of 20 ml of acetic acid, 3 times with a total of 60 ml of anhydrous ethyl ether and dried under reduced pressure. 0.72 g of diethyl 9-ethoxycarbonylmethyl-4-oxo-4,5-dihydro-10H-imidazo[1,2-a]indeno[1,2-e]pyrazine-2-methylphosphonate is thus obtained in the form of a grey powder [$^1$H NMR spectrum in DMSO-$d_6$, T=300K, δ in ppm (300 MHz): 1.25 (9H, m, 3 $CH_3$), 3.40 (2H, d, J=19 Hz, $PCH_2$), 3.80 (2H, s, $CH_2$), 4.00 (2H, s, $CH_2$), 4.10 (4H, m, 2 $OCH_2$), 7.20 (1H, d, J=8 Hz, arom. CH), 7.40 (1H, t, J=8 Hz, arom. CH), 7.80 (2H, m, arom. and imidazole CH)].

A solution of 0.7 g of diethyl 9-ethoxycarbonylmethyl-4-oxo-4,5-dihydro-10H-imidazo[1,2-a]indeno[1,2-e]pyrazine-2-methylphosphonate in 18 ml of a 6 N aqueous hydrochloric acid solution and stirred at boiling temperature for 16 hours and then cooled to a temperature close to 20° C. The solid is separated by filtration, washed 3 times with a total of 60 ml of distilled water, 4 times with a total of 80 ml of acetone, 4 times with a total of 120 ml of anhydrous ethyl ether and dried under reduced pressure at 60° C. 0.4 g of 9-carboxymethyl-4-oxo-4,5-dihydro-10H-imidazo[1,2-a]indeno[1,2-e]pyrazine-2-methylphosphonic acid is thus obtained in the form of a beige powder melting above 260° C. [$^1$H NMR spectrum in $D_2O$+NaOD, T=300K, δ in ppm (250 MHz): 3.05 (2H, d, J=19 Hz, $PCH_2$), 3.30 (2H, s, $CH_2$), 3.40 (2H, s, $CH_2$), 6.90 (1H, d, J=8 Hz, arom. CH), 7.22 (1H, t, J=8 Hz, arom. CH), 7.38 (1H, d, J=2 Hz, imidazole CH), 7.50 (1H, d, J=8 Hz, arom. CH)].

The diethyl 1-(4-ethoxycarbonylmethyl-1-oxoindan-2-yl)-2-ethoxycarbonylimidazole-4-methylphosphonate can be prepared in the following manner: 4.5 g of potassium carbonate are added to a solution of 1.95 g of diethyl 2-ethoxycarbonylimidazole-4-methylphosphonate in 35 ml of acetone. The stirred suspension is maintained at boiling temperature and a solution of 1.9 g of ethyl (2-bromo-1-oxoindan-4-yl)acetate in 10 ml of acetone is then added dropwise over 10 minutes. After stirring for 2 hours, the boiling solution is filtered and the filtrate is concentrated to dryness under reduced pressure at 40° C. The product obtained (3.2 g) is chromatographed on a neutral silica gel, eluting with ethyl acetate and then with a mixture of ethyl acetate and methanol (95-5 by volume). The fractions containing the expected product are combined and concentrated to dryness under reduced pressure and 2.15 g of diethyl 1-(4-ethoxycarbonylmethyl-1-oxoindan-2-yl)-2-ethoxycarbonylimidazole-4-methylphosphonate are thus obtained melting at 129° C. [$^1$H NMR spectrum in DMSO-$d_6$, T=300K, δ in ppm (250 MHz): between 1.10 and 1.40 (12H, m, 4 $CH_3$), 3.25 (2H, d, J=19 Hz, $PCH_2$), 3.27 and 3.78 (1H each, m, $CH_2$), 3.90 (2H, s, $CH_2CO$), between 4.00 and 4.30 (8H, m, 4 $OCH_2$), 5.90 (1H, dd, J=4 and 5 Hz, NCH), 7.50 (1H, d, J=2 Hz, imidazole CH), 7.55 (1H, t, J=8 Hz, arom. CH), 7.82 (2H, d, J=8 Hz, 2 arom. CH)].

EXAMPLE 7

1.54 g of anmonium acetate are introduced into a suspension of 1.03 g of diethyl 1-[1-oxo-4-(2-oxo-2-phenylethoxycarbonylmethyl)indan-2-yl]imidazole-2,4-dicarboxylate in 7.2 ml of acetic acid under an argon atmosphere. The reaction medium is heated at reflux for 4 hours and filtered while hot on sintered glass. The solid residue obtained is washed with twice water and then dried under reduced pressure at 60° C. 0.4 g of ethyl 9-(4-phenyl-1H-imidazol-2-ylmethyl)-4,5-dihydro-4-oxo-10H-imidazo[1,2-a]indeno[1,2-e]pyrazine-2-carboxylate is thus obtained in the form of a grey solid melting at a temperature greater than 260° C.

A mixture of 0.4 g of ethyl 9-(4-phenyl-1H-imidazol-2-ylmethyl)-4,5-dihydro-4-oxo-10H-imidazo[1,2-a]indeno[1,2-e]pyrazine-2-carboxylate and 12.5 ml of acetic acid and 2.5 ml of 6 N hydrochloric acid is heated for 24 hours at a temperature close to 100° C. The reaction medium is filtered while hot on sintered glass and the solid residue obtained is washed with three times water and then dried under reduced pressure at 60° C. 0.23 g of 9-(4-phenyl-1H-imidazol-2-ylmethyl)-4,5-dihydro-4-oxo-10H-imidazo[1,2-a]indeno[1,2-e]pyrazine-2-carboxylic acid is thus obtained in the form of a white solid melting at a temperature greater than 260° C. (Analysis: $C_{24}H_{17}N_5O_3$, 3.96 $H_2O$, 0.91 $C_2H_4O_2$: % calculated C: 68.07, H: 4.05, N: 16.54, % found C: 68.1, H: 4.1, N:16.5).

The diethyl 1-[1-oxo-4-(2-oxo-2-phenylethoxycarbonylmethyl)indan-2-yl]imidazole-2,4-dicarboxylate can be obtained in the following manner: a solution of 1.8 g of (2-oxo-2-phenyl)ethyl ester of (2-bromo-1-oxoindan-4-yl)acetic acid in 45 ml of acetone is added dropwise, under an argon atmosphere, to a suspension of 4.3 g of diethyl imidazole-2,4-dicarboxylate, 1.1 g of potassium carbonate and 25 ml of acetone. After stirring for 24 hours at a temperature close to 20° C., the reaction medium is filtered on sintered glass and the resulting solid is washed three times with water, and then dried under reduced pressure at 60° C. 2.63 g of diethyl 1-[1-oxo-4-(2-oxo-2-phenylethoxycarbonylmethyl)indan-2-yl]imidazole-2,4-dicarboxylate are thus obtained in the form of a cream-coloured solid melting at 180° C.

The (2-oxo-2-phenyl)ethyl ester of (2-bromo1-oxoindan-4-yl)acetic acid can be obtained in the following manner: 0.8 ml of hydrobromic acid is added to 12.5 g of (2-oxo-2-phenyl)ethyl ester of (1-oxoindan-4-yl)acetic acid in 200 ml of acetic acid. 2.35 ml of bromine are added dropwise to this solution cooled to a temperature close to 13° C. The reaction medium is allowed to return to a temperature close to 20° C. and the reaction is continued for 2 hours. This operation is repeated twice. The two reaction media are combined, poured into a mixture of 400 g of ice and 400 ml of water and taken up in a litre of diethyl ether. The organic phase is concentrated and the resulting brown oil is taken up in 500 ml of diethyl ether. After decantation, the ethereal phase is concentrated and purified by chromatography on silica with a cyclohexane-methanol (7-3 by volume) mixture as eluent. 9.5 g of (2-oxo-2-phenyl)ethyl ester of (2-bromo-1-oxoindan-4-yl)acetic acid are thus obtained in the form of a yellow oil used as is in the subsequent syntheses.

The (2-oxo-2-phenyl)ethyl ester of (1-oxoindan-4-yl) acetic acid can be obtained in the following manner: a solution of 18.92 g of bromoacetophenone in 47 ml of ethyl acetate is added dropwise and at a temperature maintained at around 20° C. to a solution of 18 g of (1-oxoindan-4-yl) acetic acid, 13.2 ml of triethylamine in 190 ml of ethyl acetate. The reaction medium is stirred for 22 hours at a temperature close to 25° C. and then filtered on sintered glass. The resulting solution is washed successively with 200 ml of water, 200 ml of an aqueous sulphuric acid solution at 5%, 200 ml of an aqueous sodium bicarbonate solution at 5% and 200 ml of salt water. After concentration of the organic phase, a yellow oil is obtained which crystallizes rapidly. The solid is ground with distilled water, and then dried under reduced pressure at 60° C. 25 g of (2-oxo-2-phenyl)ethyl ester of (1-oxoindan-4-yl)acetic acid are thus obtained in the form of a yellow solid melting at 74° C.

EXAMPLE 8

A solution of 0.8 g of (E)-3-(9-carboxymethyl-4-oxo-5,10-dihydroimidazol1,2-a]indeno[1,2-e]pyrazin-2-yl)acrylic acid in 18 ml of a 0.32 N aqueous sodium hydroxide solution is hydrogenated in the presence of 0.04 g of 10% palladized charcoal for 12 hours at a temperature close to 40° C. and at a pressure close to 5 bar. The reaction medium is filtered and then acidified with 1N hydrochloric acid up to pH 3. The precipitate produced is washed with 2×5 ml of distilled water, and then with 2×5 ml of acetone and finally dried under vacuum (1 mm Hg; 0.13 kPa) at about 60° C. 0.4 g of 3-(9-carboxymethyl-4-oxo-5,10-dihydroimidazo[1,2-a] indeno[1,2-e]pyrazin-2-yl)propionic acid is obtained in the form of a beige solid melting above 260° C. [Analysis: $C_{18}H_{15}N_3O_5$, 1.3 $H_2O$, % calculated C: 61.19, H: 4.28, N: 11.89, O: 22.64, % found C: 60.8, H: 4.4, N: 12.0, O: 22.1].

EXAMPLE 9

A mixture of 0.3 g of ethyl (E)-4-(2-ethoxycarbonylvinyl)-1-(ethoxycarbonylmethyl-1-oxoindan-2-yl)imidazole-2-carboxylate, 7 ml of acetic acid and 5 g of ammonium acetate is heated at reflux for 1 hour. The reaction mixture is supplemented with 7 ml of distilled water and the insoluble matter is isolated by filtration, washed with 2×5 ml of distilled water and then 2×5 ml of acetone. After drying under vacuum (1 mm Hg, 0.13 kPa) at about 20° C., 0.15 g of ethyl (E)-3-(9-carboxymethyl-4-oxo-5,10-dihydroimidazo[1,2-a]indeno[1,2-e]pyrazin-2-yl) acrylate is obtained in the form of a brown solid melting above 260° C., used as is in the subsequent syntheses [$^1$H NMR spectrum in DMSO-$d_6$, T=300K, δ in ppm (250 MHz): 1.22 (3H, t, J=6 Hz, $CH_3$), 1.30 3H, t, J=6 Hz, $CH_3$), 3.87 (2H, s, $CH_2$), 4.00 (2H, s, $CH_2$), 4.15 (2H, q, J=6 Hz, $OCH_2$), 4.25 (2H, q, J=6 Hz, $OCH_2$), 6.70 (1H, d, J=16 Hz, ethylenic CH), 7.28 (1H, d, J=7 Hz, arom. CH), 7.42 (1H, t, J=7 Hz, arom. CH), 7.70 (1H, d, J=16 Hz, ethylenic CH), 7.84 (1H, d, J=7 Hz, arom. CH), 8.40 (1H, s, imidazole CH), 12.00 (1H, broad s, NHCO)].

A mixture of 1.45 g of ethyl (E)-3-(9-carboxymethyl-4-oxo-5,10-dihydroimidazo[1,2-a]indeno[1,2-e]pyrazin-2-yl) acrylate, 19 ml of concentrated hydrochloric acid and 78 ml of acetic acid is heated at reflux for 48 hours. The reaction mixture is filtered and the solid is washed with 2×20 ml of distilled water and then with 2×10 ml of acetone and finally dried under vacuum (1 mm Hg; 0.13 kPa) at about 60° C. 0.94 g of (E)-3-(9-carboxymethyl-4-oxo-5,10-dihydroimidazo[1,2-a]indeno[1,2-e]pyrazin-2-yl)acrylic acid is obtained in the form of a beige solid melting above 260° C. [Analysis: $C_{18}H_{13}N_3O_5$, 0.89 HCl, 0.91 $H_2O$, % calculated C: 61.54, H: 3.73, N: 11.96, O: 22.77, % found C: 61.8, H: 3.4, N: 11.9].

The ethyl (E)-4-(2-ethoxycarbonylvinyl)-1-(7-ethoxycarbonylmethyl-3-oxoindan-2-yl)imidazole-2-carboxylate can be prepared in the following manner: a mixture of 0.3 g of ethyl (E)-4(5)-(2-ethoxycarbonylvinyl)-1H-imidazole-2-carboxylate, 6 ml of acetone and 0.86 g of potassium carbonate is heated to the reflux temperature under an argon atmosphere. A solution of 0.37 g of ethyl (2-bromo-1-oxoindan-4-yl)acetate in 4 ml of acetone is then added and the refluxing is continued for 1 hour. The reaction medium is filtered and the filtrate is evaporated in a rotary evaporator to give 0.5 g of a black lacquer, which is purified by chromatography on silica, eluting with a dichloromethane-methanol (99.5-0.5 by volume) mixture. 0.2 g of ethyl (E)-4-(2-ethoxycarbonylvinyl)-1-(7-ethoxycarbonylmethyl-3-oxoindan-2-yl)imidazole-2-carboxylate is thus obtained in the form of a brown foam melting at 53° C. used as is in the subsequent syntheses [$^1$H NMR spectrum in DMSO-$d_6$, T=300K, δ in ppm (300 MHz): 1.18 (3H, t, J=6 Hz, $CH_3$), 1.22 (3H, t, J=6 Hz, $CH_3$), 1.30 (3H, t, J=6 Hz, $CH_3$), 3.35 and 3.82 (1H each, respectively dd, J=17 and 4 Hz, and dd, J=6 and 17 Hz, $PhCH_2$), 3.90 (2H, s, $CH_2CO$), 4.20 (6H, m, 3 $OCH_2$), 5.92 (1H, dd, J=6 and 4 Hz, CHN), 6.55 (1H, d, J=16 Hz, ethylenic CH), 7.58 (1H, t, J=7 Hz, arom. CH), 7.60 (1H, d, J=16 Hz, ethylenic CH), 7.75 (2H, d, J=7 Hz, 2 arom. CH), 8.05 (1H, s, imidazole CH)].

EXAMPLE 10

A mixture of 0.6 g of diethyl 1-[7-(diethoxyphosphorylmethyl)-3-oxoindan-2-yl]imidazole 2,4-carboxylate, 18 ml of acetic acid and 9.4 g of ammonium acetate is heated at reflux for 3 hours. The reaction mixture is supplemented with 20 ml of distilled water and the insoluble matter is isolated by filtration, washed with 2×5 ml of distilled water and then 2×5 ml of acetone. After drying under vacuum (1 mm Hg, 0.13 kPa) at close to 20° C., 0.26 g of ethyl 9-(diethoxyphosphorylmethyl)-4-oxo-5,10-dihydroimidazo[1,2-a]indeno[1,2-e]pyrazine-2-carboxylate is obtained in the form of a brown solid melting above 260° C., used as is in the subsequent syntheses [$^1$H NMR spectrum in DMSO-$d_6$, T=300K, δ in ppm (300 MHz): 1.15 (6H, t, J=6 Hz, 2 $CH_3$), 1.35 (3H, t, J=6 Hz, $CH_3$), 3.35 (2H, d, J=22 Hz, $PCH_2$), 3.98 (4H, q, J=6 Hz, 2 $OCH_2$), 4.10 (2H, S, $CH_2$), 4.35 (2H, q, J=6 Hz, $OCH_2$), 7.25 (1H, d, J=7 Hz, arom. CH), 7.40 (1H, t, J=7 Hz, arom. CH), 7.80 (1H, d, J=7 Hz, arom. CH), 8.65 (1H, s, imidazole CH), 12.60 (1H, broad s, NHCO)].

A mixture of 0.6 g of ethyl 9-(diethoxyphosphorylmethyl)-4-oxo-5,10-dihydroimidazo [1,2-a]indeno[1,2-e]pyrazine-2-carboxylate, 30 ml of hydrobromic acid at 30% in acetic acid and 10 ml of distilled water is heated at reflux for 2 hours. The reaction mixture is filtered and the solid is washed with 3×20 ml of distilled water, and then with 2×10 ml of acetone and finally dried under vacuum (1 mm Hg, 0.13 kPa) at close to 40° C. 0.3 g of 4-oxo-9-phosphonomethyl-5,10-dihydroimidazo[1,2] indeno[1,2-e]pyrazine-2-carboxylic acid is obtained in the form of a beige solid melting above 260° C. [Analysis: $C_{15}H_{12}N_3O_6P$, 0.09 HBr, 0.38 HCl, 1.54 $H_2O$, % calculated C: 49.87, H: 3.3, N: 11.63, O: 26.57, P: 8.57, % found C: 49.8, H: 3.4, N: 11.11].

The ethyl 1-[7-(diethyoxyphosphorylmethyl)-3-oxoindan-2-yl]imidazole-2,4-dicarboxylate can be prepared in the following manner: a mixture of 0.3 g of ethyl 1H-imidazole-2,4(5)-dicarboxylate, 20 ml of acetone and 0.59 g of potassium carbonate is heated to the reflux temperature under an argon atmosphere. A solution of 1.0 g of diethyl 2-bromo-1-oxoindan-4-ylmethylphosphonate in 10 ml of acetone is then added and the refluxing is continued for 2 hours. The reaction medium is filtered and the filtrate is evaporated in a rotary evaporator. The evaporation residue is purified by chromatography on silica, eluting with an ethyl acetate-acetone mixture (95-5 by volume). 0.76 g of ethyl 1-[7-(diethoxyphosphorylmethyl)-3-oxoindan-2-yl]imidazole-2,4-dicarboxylate is thus obtained in the form of a yellow oil [$^1$H NMR spectrum in DMSO-$d_6$, T=300K, δ in ppm (250 MHz): 1.20 (9H, m, 3 $CH_3$), 1.35 (3H, t, J=6 Hz, $CH_3$), 3.40 (3H, m, HCH and $PCH_2$), between 3.80 and 4.40 (9H, m, HCH and 4 $OCH_2$), 5.90 (1H, dd, J=5 and 8 Hz, NCH), 7.55 (1H, t, J=7 Hz, arom. CH), 7.70 (1H, m, arom. CH), 8.40 (1H, s, imidazole CH)].

The diethyl 2-bromo-1-oxoindan-4-ylmethylphosphonate can be prepared in the following manner: a mixture of 0.37 g of diethyl 1-oxoindan-4-ylmethylphosphonate and 0.5 g of pyridinium perbromide monohydrate in 5 ml of acetone is heated at a temperature close to 50° C. for one hour and thirty minutes. The reaction medium is concentrated in a rotary evaporator. The evaporation residue is taken up in 20 ml of diethyl ether, the organic phase is washed with 2×10 ml of distilled water and then dried over magnesium sulphate and concentrated in a rotary evaporator. 0.46 g of diethyl 2-bromo-1-oxoindan-4-ylmethylphosphonate is obtained in the form of a yellow oil [$^1$H NMR spectrum in DMSO-$d_6$, T=300K, δ in ppm (250 MHz): 1.20 (6H, m, 2 $CH_3$), 3.40 and 3.90 (1H each, m, $CH_2$), 3.48 (2H, d, J=15 Hz, $PCH_2$), 4.00 (4H, m, $OCH_2$), 5.10 (1H, dd, J=6 and 2 Hz, CHBr), 7.50 (1H, t, J=7 Hz, arom. CH), 7.70 (2H, d, J=7 Hz, 2 arom. CH)].

The diethyl 1-oxoindan-4-ylmethylphosphonate can be prepared in the following manner: a mixture of 0.5 g of 4-(bromomethyl)indan-1-one, 0.9 g of triethyl phosphate and 5 ml of xylene is heated at reflux for 5 hours. The reaction medium is concentrated in a rotary evaporator and then the residue is purified by chromatography on silica, eluting with an ethyl acetate-petroleum ether (85-15 by volume) mixture. 0.4 g of diethyl (2-bromo-1-oxoindan-4-yl)methylphosphonate is obtained in the form of a colourless oil [$^1$H NMR spectrum in DMSO-$d_6$, T=300K, δ in ppm (250 MHz): 1.20 (6H, t, J=6 Hz, 2 $CH_3$), 2.70 (2H, m, $CH_2CO$), 3.20 (2H, m, $CH_2$), 3.38 (2H, d, J=22 Hz, $PCH_2$), 4.00 (2H, q, J=6 Hz, $OCH_2$), 7.45 (1H, t, J=7 Hz, arom. CH), 7.60 (2H, m, 2 arom. CH)].

The 4-(bromomethyl)indan-1-one can be prepared according to Agric. Biol. Chem. 42(7), 1365–73 (1978).

EXAMPLE 11

4.38 g of ammonium acetate are added to a solution of 2.9 g of ethyl 1-(4-carbethoxymethyl-1-oxoindan- 2-yl)-4-(4-carbethoxyphenyl)imidazole-2-carboxylate in 25 ml of acetic acid and the mixture is stirred for 2 hours at boiling temperature and again for 2 hours after addition of 1 g of ammonium acetate. After cooling to 60° C., the insoluble matter is separated by filtration, washed 3 times with a total of 45 ml of acetic acid, 3 times with a total of 90 ml of ethyl ether and dried under reduced pressure (0.5 mm Hg; 0.07 kPa) at 60° C. 1.8 g of ethyl 2-(4-carbethoxyphenyl)-4-oxo-4,5-dihydro-10H-imidazo[1,2-a]indeno[1,2-e]pyrazine-9-acetate are thus obtained in the form of a beige solid which decomposes without melting above 260° C. [$^1$H NMR spectrum in DMSO-$d_6$, T=300K, δ in ppm (300 MHz): 1.20 (3H, t, J=6 Hz, $CH_3$), 1.35 (3H, t, J=6 Hz, $CH_3$), 3.85 (2H, s, $CH_2CO$), 4.00 (2H, s, $CH_2$), 4.12 (2H, q, J=6 Hz, $OCH_2$), 4.35 (2H, q, J=6 Hz, $OCH_2$), 7.25 (1H, d, J=7 Hz, arom. CH), 7.40 (1H, t, J=7 Hz, arom. CH), 7.85 (1H, d, J=7 Hz, arom. CH), 8.05 and 8.15 (2H each, d, J=7 Hz, $PhCO_2H$.), 8.70 (1H, s, imidazole CH), 12.10 (1H, s, NHCO)].

A stirred suspension of 1.7 g of ethyl 2-(4-carbethoxyphenyl)-4-oxo-4,5-dihydro-10H-imidazo[1,2-a]indeno[1,2-e]pyrazine-9-acetate in 40 ml of a 6 N aqueous hydrochloric acid solution is maintained at boiling temperature for 24 hours. After cooling, the insoluble matter is separated by filtration, washed 3 times with a total of 60 ml of distilled water and dried under reduced pressure (0.5 mm Hg; 0.07 kPa) at 45° C. 1.4 g of product thus obtained (out of 1.46 g obtained in total) is dissolved in 15 ml of a 1 N aqueous sodium hydroxide solution and the solution is stirred for 16 hours at 20° C. After addition of 10 ml of distilled water, the solution is acidified with a 10 N aqueous hydrochloric acid solution. The insoluble matter produced is separated by filtration, washed 3 times with a total of 30 ml of distilled water, 3 times with a total of 30 ml of acetone and dried under reduced pressure (0.5 mm Hg; 0.07 kPa) at 60° C. 1.2 g of 2-(4-carboxyphenyl)-4-oxo-4,5-dihydro-10H-imidazo[1,2-a]indeno[1,2-e]pyrazine-9-acetic acid hydrochloride are thus obtained in the form of a beige solid which decomposes without melting above 260° C. [$^1$H NMR spectrum in DMSO-$d_6$, T=300K, δ in ppm (300 MHz): 3.75 (2H, s, $CH_2CO$), 4.00 (2H, s, $CH_2$), 7.25 (1H, d, J=7 Hz, arom. CH), 7.40 (1H, t, J=7 Hz, arom. CH), 7.80 (1H, d, J=7 Hz, arom. CH), 8.05 and 8.15 (2H each, d, J=7 Hz, $PhCO_2Et$), 8.70 (1H, s, imidazole CH), 12.50 (1H, s, NHCO)].

The ethyl 1-(4-carbethoxymethyl-1-oxoindan-2-yl)-4-(4-carbethoxyphenyl)imidazole-2-carboxylate can be prepared in the following manner: 4.48 g of potassium carbonate are added to a solution of 1.87 g of ethyl 4(5)-(carbethoxyphenyl)-1H-imidazole-2-carboxylate in 50 ml of acetone. The stirred mixture is heated at boiling temperature and then a solution of 2.07 g of ethyl (2-bromo-1-oxoindan-4-yl)acetate in 15 ml of acetone is added dropwise over 5 minutes. The stirring at boiling temperature is continued for 3 hours and, after cooling to 20° C., the insoluble matter is removed by filtration and the filtrate is concentrated to dryness under reduced pressure (15 mm Hg; 2 kPa) at 40° C. The product obtained is chromatographed on a neutral silica gel column, eluting with ethyl acetate. 2.9 g of ethyl 1-(4-carbethoxymethyl-1-oxoindan-2-yl)-4-(4-carbethoxyphenyl)imidazole-2-carboxylate are thus obtained in the form of a light brown foam (Rf=0.8; thin-layer chromatography on silica gel, eluent: ethyl acetate).

EXAMPLE 12

A stirred suspension of 1 g of ethyl 2-(3-cyanophenyl)-4-oxo-4,5-dihydro-10H-imidazo[1,2-a]indeno[1,2-e]pyrazine-9-acetate in 50 ml of a concentrated aqueous hydrochloric acid solution is maintained at boiling temperature for 48 hours. After cooling, the insoluble matter is separated by filtration, washed 3 times with a total of 30 ml of distilled water and dried under reduced pressure (0.5 mm Hg; 0.07 kPa) at 60° C. 0.8 g of 2-(3-carboxyphenyl)-4- oxo-4,5-dihydro-10H-imidazo[1,2-a]indeno[1,2-e]pyrazine-9-acetic acid hydrochloride is thus obtained in the form of a beige powder which decomposes without melting above 260° C. [$^1$H NMR spectrum in DMSO-$d_6$, T=300K, δ in ppm (300 MHz): 3.80 (2H, s, CH$_2$CO), 4.00 (2H, s, CH$_2$), 7.30 (1H, d, J=7 Hz, arom. CH), 7.40 (1H, t, J=6 Hz, arom. CH), 7.65 (1H, t, J=6 Hz, arom. CH), 7.88 (1H, d, J=7 Hz, arom. CH), 8.00 and 8.25 (1H each, d, J=6 Hz, 2 arom. CH), 8.62 and 8.88 (1H each, s, 2 arom. CH), 12.80 (1H, s, NHCO)].

The ethyl 2-(3-cyanophenyl)-4-oxo-4,5dihydro-10H-imidazo[1,2-a]indeno[1,2-e]pyrazine-9-acetate can be obtained in the following manner: 8.08 g of ammonium acetate are added to a solution of 4.8 g of ethyl 1-(4-carbethoxymethyl-1-oxoindan-2-yl)-4-(3cyanophenyl)imidazole-2-carboxylate in 50 ml of acetic acid and the mixture is stirred for 3 hours at boiling temperature and then again for 2 hours after addition of 2.4 g of ammonium acetate. After cooling to 20° C., the insoluble matter is separated by filtration, washed twice with a total of 20 ml of acetic acid, 3 times with a total of 60 ml of ethyl ether and dried under reduced pressure (0.5 mm Hg; 0.07 kPa) at 50° C. 2.76 g of ethyl 2-(3-cyanophenyl)-4-oxo-4,5-dihydro-10H-imidazo[1,2-a]indeno[1,2-e]pyrazine-9-acetate are thus obtained in the form of a grey powder which decomposes without melting above 260° C. [$^1$H NMR spectrum in DMSO-$d_6$, T=300K, δ in ppm (300 MHz); 1.20 (3H, t, J=6 Hz, CH$_3$), 3.87 (2H, s, CH$_2$CO), 4.00 (2H, s, CH$_2$), 4.13 (2H, q, J=6 Hz, OCH$_2$), 7.25 (1H, d, J=7 Hz, arom. CH), 7.40 and 7.70 (1H each, t, J=7 Hz, 2 arom. CH), 7.80 (2H, d, J=7 Hz, 2 arom. CH), 8.33 (1H, d, J=7 Hz, arom. CH), 8.42 (1H, s, arom. CH), 8.72 (1H, s, imidazole CH)].

The ethyl 1-(4-carbethoxymethyl-1-oxoindan-2-yl)-4-(3-cyanophenyl)imidazole-2-carboxylate can be prepared in the following manner: 8.97 g of potassium carbonate are added to a solution of 3.32 g of ethyl 4(5)-(3-cyanophenyl)-1H-imidazole-2-carboxylate in 100 ml of acetone. The stirred mixture is heated at boiling temperature and then a solution of 4.15 g of ethyl (2-bromo-1-oxoindan-4-yl)acetate in 30 ml of acetone is then added dropwise over 5 minutes. The stirring at boiling temperature is continued for 4 hours, the insoluble matter is removed by filtration while hot and the filtrate is concentrated to dryness under reduced pressure (15 mm Hg; 2 kPa) at 40° C. The product obtained is chromatographed on a neutral silica gel column, eluting with ethyl acetate. 4.86 g of ethyl 1-(4-carbethoxymethyl-1-oxoindan-2-yl)-4-(3-cyanophenyl)imidazole-2-carboxylate are thus obtained in the form of a brown foam ($^1$H NMR spectrum in DMSO-$d_6$, T=300K, δ in ppm (300 MHz); 1.15 (6H, t, J=6 Hz, 2 CH$_3$), 3.30 and 3.80 (1H each, m, CH$_2$), 3.85 (2H, s, CH$_2$CO), between 4.50 and 4.30 (4H, m, 2 OCH$_2$), 5.95 (1H, m, NCH), between 7.50 and 7.90 (5H, m, 5 arom. CH), 8.20 (1H, d, J=6 Hz, arom. CH), 8.25 (1H, s, arom. CH), 8.30 (1H, s, imidazole H)].

The ethyl 4(5)-(3-cyanophenyl)-1H-imidazole-2-carboxylate can be obtained in the following manner: a solution of 7.4 g of triethyloxonium tetrafluoroborate in 25 ml of methylene chloride is added dropwise at 20° C. over 10 minutes to a solution of 3.45 g of ethyl thiooxamate in 130 ml of methylene chloride. The mixture is stirred for 16 hours at a temperature close to 20° C. and then concentrated to dryness under reduced pressure (15 =m Hg; 2 kPa) at 45° C. The product obtained (8.9 g) is dissolved in 25 ml of acetic acid and 5.1 g of 3-glycylbenzonitrile hydrochloride and then 4.26 g of anhydrous sodium acetate are added. The mixture is stirred for 3 hours 30 minutes at 95° C. and is then concentrated to dryness under reduced pressure (15 mm Hg; 2 kPa) at 50° C. The product obtained is suspended twice in a total of 100 ml of methylene chloride and, after filtration, the filtrates are combined and concentrated to dryness under reduced pressure (15 mm Hg; 2 kPa) at 50° C. The product obtained is dissolved in 300 ml of boiling ethyl acetate and, after filtration of the solution while hot, cooling and storage for 1 hour at a temperature close to 5° C., the crystals produced are separated by filtration and dried. 3.3 g of ethyl 4(5)-(3-cyanophenyl)-1H-imidazole-2-carboxylate are thus obtained melting at 176° C.

The 3-glycylbenzonitrile hydrochloride can be prepared according to the method described in European Patent 52442.

EXAMPLE 13

3.07 g of ammonium acetate are added to a solution of 2.15 g of ethyl 1-(4-carbethoxymethyl-1-oxoindan-2-yl)-4-(2-carbethoxyphenyl)imidazole-2-carboxylate in 25 ml of acetic acid and the mixture is stirred for 4 hours 30 minutes at boiling temperature and then concentrated to dryness under reduced pressure (15 mm Hg; 2 kPa) at 50° C. The product obtained is dissolved in 100 ml of methylene chloride and the solution is washed 3 times with a total of 150 ml of distilled water, dried over anhydrous sodium sulphate and concentrated to dryness under reduced pressure (15 mm Hg; 2 kPa) at 50° C. The product obtained is washed 4 times with a total of 200 ml of ethyl ether and dried under reduced pressure (0.5 mm Hg; 0.07 kPa) at 60° C. 1.4 g of ethyl 2-(2-carbethoxyphenyl)-4-oxo-4,5-dihydro-10H-imidazo[1,2-a]indeno[1,2-e]pyrazine-9-acetate are thus obtained in the form of a grey powder which decomposes without melting above 260° C. [$^1$H NMR spectrum in DMSO-$d_6$, T=300K, δ in ppm (250 MHz): 1.15 (3H, t, J=6 Hz, CH$_3$), 1.25 (3H, t, J=6 Hz, CH$_3$), 3.87 (2H, s, CH$_2$CO), 4.00 (2H, s, CH$_2$), 4.15 (2H, q, J=6 Hz, OCH$_2$), 4.27 (2H, q, J=6 Hz, OCH$_2$), 7.25 (1H, d, J=7 Hz, arom. CH), 7.42 and 7.50 (1H each, t, J=7 Hz, 2 arom. CH), 7.65 (2H, m, 2 arom. CH), 7.85 (2H, m, 2 arom. CH), 8.30 (1H, s, imidazole CH), 12.50 (1H, s, NHCO)].

A stirred solution of 1.3 g of ethyl 2-(2-carbethoxyphenyl)-4-oxo-4,5-dihydro-10H-imidazo[1,2-a]indeno[1,2-e]pyrazine-9-acetate in 45 ml of a 12 N aqueous hydrochloric acid solution is maintained at boiling temperature for 64 hours. After cooling, the insoluble matter is separated by filtration, washed 3 times with a total of 45 ml of distilled water and dried under reduced pressure (0.5 mm Hg; 0.07 kPa) at 45° C. 0.9 g of 2-(2-carboxyphenyl)-4-oxo-4,5-dihydro-10H-imidazo[1,2-a]indeno[1,2-e]pyrazine-9-acetic acid chloride is thus obtained in the form of a dark grey solid which decomposes without melting above 260° C. [$^1$H NMR spectrum in DMSO-$d_6$, T=300K, δ in ppm (250 MHz); 3.75 (2H, s, CH$_2$), 4.05 (2H, s, CH$_2$), 7.25 (1H, d, J=7 Hz, arom. CH), 7.40 (1H, t, J=7 Hz, arom. CH), between 7.50 and 8.10 (5H, m, 5 arom. CH), 8.45 (1H, s, imidazole CH), 13.00 (1H, broad s, NHCO)].

The ethyl 1-(4-carbethoxymethyl-1-oxoindan-2-yl)-4-(2-carbethoxyphenyl)imidazole-2-carboxylate can be prepared in the following manner: 4.14 g of potassium carbonate are added to a solution of 1.55 g of ethyl 4(5)-(2-carbethoxyphenyl)-1H-imidazole-2-carboxylate in 50 ml of acetone. The stirred mixture is heated at boiling temperature and then a solution of 1.8 g of ethyl (2-bromo-1-oxoindan-4-yl)acetate in 15 ml of acetone is added dropwise over 5 minutes. The stirring at boiling temperature is continued for 3 hours 30 minutes and, after cooling to 20° C., the insoluble matter is removed by filtration and the filtrate is concentrated to dryness under reduced pressure (15 mm Hg; 2 kPa) at 40° C. The product obtained is chromatographed on a neutral silica gel column, eluting with a methylene chloride-ethyl acetate (80-20 by volume) mixture. 2.28 g of ethyl 1-(4-carbethoxymethyl-1-oxoindan-2-yl)-4-(2-carbethoxyphenyl)imidazole-2-carboxylate are thus obtained in the form of an orange-coloured thick oil ($^1$H NMR spectrum in DMSO-$d_6$, T=300K, δ in ppm (300 MHz): 1.10 (9H, m, 3 $CH_3$), 3.30 and 3.75 (1H each, m, $CH_2$), 3.80 (2H, s, $CH_2CO$), between 4.00 and 4.30 (6H, m, 3 $OCH_2$), 5.85 (1H, m, CH), between 7.30 and 7.70 (7H, m, 7 arom. CH), 7.85 (1H, s, imidazole H)].

EXAMPLE 14

3 g of ammonium acetate are added, with stirring, to a solution of 2.1 g of 2-(2,4-diethoxycarbonylimidazol-1-yl)-4-benzenesulphonamidocarbonylmethylindan-1-one and 55 ml of acetic acid. The reaction medium is heated at boiling temperature for 3 hours and then cooled and poured into a mixture of 60 g of ice and 60 ml of distilled water. The suspension thus obtained is filtered on sintered glass, washed twice with 20 ml of water, 10 ml of acetone and dried under reduced pressure at 53° C. 0.92 g of ethyl 9-bezenesulphonamidocarbonylmethyl-4-oxo-4,5-dihydro-10H-imidazo[1,2-a]indeno[1,2-e]-pyrazine-2-carboxylate is thus obtained in the form of a grey solid melting above 260° C. (Analysis: $C_{24}H_{20}N_4O_6S_1$: % calculated C: 58.53, H: 4.09, N: 11.38, S: 6.54; % found C: 58.3, H: 4.1, N: 11.5, S: 6.9).

5 ml of 1 N aqueous sodium hydroxide are added dropwise to a suspension of 0.6 g of ethyl 9-bezenesulphonamidocarbonylmethyl-4-oxo-4,5-dihydro-10H-imidazo[1,2-a]indeno[1,2-e]-pyrazine-2-carboxylate in 60 ml of dioxane and 1.8 ml of distilled water. The reaction medium is kept stirring for 20 hours, filtered on sintered glass and the solid thus obtained is washed with twice 10 ml of dioxane, air dried and then dissolved in 20 ml of distilled water. 0.1 g of animal charcoal is added to this solution. After filtration, on paper, the filtrate is acidified to a pH close to 3-4 with 3.5 ml of 1 N hydrochloric acid. After allowing to stand at a temperature close to 20° C., the suspension is filtered on sintered glass. The solid thus obtained is washed with 3 times 10 ml of water and 10 ml of acetone and then dried under reduced pressure at 50° C. 0.28 g of a light beige solid is thus obtained. The filtrate is concentrated under reduced pressure at 48° C. and makes it possible to obtain 0.07 g of a white solid. These two solids are suspended in 35 ml of dioxane and 1 ml of distilled water, to which are added dropwise while the temperature is maintained at 20° C., 2.5 ml of 1 N sodium hydroxide. After stirring for 18 hours, the reaction medium is filtered on sintered glass and the resulting solid is washed with twice 10 ml of dioxane, air dried and then dissolved in 10 ml of distilled water. 2.1 ml of 1 N hydrochloric acid are added to this solution while the temperature is maintained at 20° C. After maintaining stirred for 3 hours, the suspension is filtered on sintered glass, washed with twice 5 ml of distilled water and dried under reduced pressure at 50° C. 0.28 g of 9-bezenesulphonamidocarbonylmethyl-4-oxo-4,5-dihydro-10H-imidazo[1,2-a]inden[1,2-e]-pyrazine-2-carboxylic acid is thus obtained in the form of a beige solid melting above 260° C. (Analysis: $C_{22}H_{16}N_4O_6S_1$, 1.94 $H_2O$, % calculated C: 56.90, H: 3.47, N: 12.06, S: 6.90; % found C: 56.4, H: 2.8, N: 11.9, S: 6.6).

The 2-(2,4-diethoxycarbonylimidazol-1-yl)-4-benzenesulphonamidocarbonylmethylindan-1-one can be obtained in the following manner: on the one hand, 1.95 g of 1,1'-carbonyldiimidazole are added in portions to a suspension of 2.4 g of diethyl 1-[4-(carboxymethyl)-1-oxoindan-2-yl]imidazole-2,4-dicarboxylate in 25 ml of tetrahydrofuran and the reaction medium is kept stirring at a temperature close to 20° C. for 1 hour 30 minutes. A solution A is thus obtained. On the other hand, a solution of 1.9 g of benzene sulphonamide in 15 ml of tetrahydrofuran is added dropwise to a suspension, cooled to 0° C., of 0.36 g of sodium hydride at 80% and 5 ml of tetrahydrofuran under an argon atmosphere. The reaction medium is then brought to a temperature close to 20° C. and stirred for 1 hour. This medium is again cooled to 0° C. and solution A is then added dropwise while the temperature is maintained at 0° C. The reaction medium is kept stirring at this temperature for 15 minutes and then brought to a temperature close to 20° C. and stirred for 2 hours. The reaction medium is poured into a mixture of 100 g of ice and 100 ml of water and taken up in twice 100 ml of dichloromethane. The aqueous phase is acidified up to a pH close to 4 with 4 ml of acetic acid. This phase is extracted with three times 100 ml of dichloromethane. The combined organic phases are washed with twice 100 ml of distilled water, dried over magnesium sulphate, filtered on paper and concentrated under reduced pressure at 45° C. The solid residue thus obtained is purified by chromatography on silica with ethyl acetate as eluent. 2.1 g of 2-(2,4-diethoxycarbonylimidazol-1-yl)-4-benzenesulphonamidocarbonylmethylindan-1-one are thus obtained in the form of a cream-coloured solid used as is for the rest of the synthesis.

The diethyl 1-[4-(carboxymethyl)-1-oxoindan-2-yl] imidazole-2,4-dicarboxylate can be obtained in the following manner: 6.5 g of diethyl 1-[4-(tert-butoxycarbonylmethyl)-1-oxoindan-2-yl]imidazole-2,4-dicarboxylate are added in portions to a solution of 75 ml of 6.5 N hydrochloric dioxane and the stirring is maintained for one hour at a temperature close to 20° C. The reaction medium is concentrated under reduced pressure at 43° C. and the oily residue thus obtained is stirred for 2 hours in the presence of 150 ml of diethyl ether. The suspension thus obtained is filtered on sintered glass, washed with twice 25 ml of diethyl ether and air dried. 5.1 g of diethyl 1-[4-(carboxymethyl)-1-oxoindan-2-yl]imidazole-2,4-dicarboxylate are thus obtained in the form of a cream-coloured solid melting at 180° C.

The diethyl 1-[4-(tert-butoxycarbonylmethyl)-1-oxoindan-2-yl]imidazole-2,4-dicarboxylate can be obtained in the following manner: a suspension of 3.1 g of diethyl imidazole-2,4-dicarboxylate, 11 g of potassium carbonate and 90 ml of acetone is heated to the reflux temperature, with stirring. A solution of 5.2 g of tert-butyl (2-bromo-1-oxoindan-4-yl)acetate in 60 ml of acetone is then added dropwise over ten minutes. After stirring for 4 hours at reflux, the reaction medium is cooled and concentrated under reduced pressure at 40° C. The brown solid residue thus obtained is then taken up in 600 ml of distilled water and 600 ml of dichloromethane. After decantation, the aqueous phase is taken up in twice 600 ml of dichloromethane. The combined organic phases are washed with 600 ml of distilled water, dried over magnesium sulphate, filtered on paper and concentrated under reduced pressure at 35° C. 6.6 g of diethyl 1-[4-(tert-butoxycarbonylmethyl)-1-oxoindan-2-yl]imidazole-2,4-dicarboxylate are thus obtained in the form of a light chestnut-coloured solid melting at 175° C.

The tert-butyl (2-bromo-1-oxoindan-4-yl)acetate can be obtained in the following manner: a suspension of 9.6 g of (2-bromo-1-oxoindan-4-yl)acetic acid in 175 ml of toluene is heated at 80° C., with stirring, until dissolution is obtained. At this temperature, 31 ml of N,N-dimethylformamide di-tertbutyl acetal are added dropwise over 10 minutes and the stirring is maintained for 15 minutes. After cooling, the reaction medium is poured over 700 ml of distilled water and 480 ml of ethyl acetate are added. After decantation, the organic phase is washed with twice 300 ml of saturated sodium hydrogen carbonate solution and then with twice 300 ml of distilled water. The organic phase is dried over magnesium sulphate, filtered on paper and concentrated under reduced pressure at 40° C. The residue thus obtained is purified by chromatography on silica with dichloromethane as eluent. 4.2 g of tert-butyl (2-bromo-1-oxoindan-4-yl)acetate are thus obtained in the form of a yellow solid melting at 64° C.

The (2-bromo-1-oxoindan-4-yl)acetic acid can be obtained in the following manner: 4 ml of hydrobromic acid at 47% are added to a solution of 38 g of (1-oxoindan-4-yl)acetic acid in 800 ml of acetic acid. 11 ml of bromine are added dropwise and over 10 minutes to this solution cooled to a temperature close to 15° C. and then the reaction medium is kept stirring for one hour at a temperature close to 15° C. The reaction medium is allowed to return to a temperature close to 20° C. and the reaction is continued for 2 hours. The reaction medium is poured into a mixture of 800 g of ice and 800 ml of water and then filtered on sintered glass. The filtrate is taken up in three times 800 ml of dichloromethane and the combined organic phases are washed with twice 800 ml of distilled water, dried over magnesium sulphate, filtered on paper and concentrated under reduced pressure at 50° C. The solid residue thus obtained is triturated in 240 ml of diisopropyl ether, filtered on sintered glass and air dried. 45.4 g of (2-bromo-1-oxoindan-4-yl)acetic acid are thus obtained in the form of a cream-coloured solid melting at 120° C.

EXAMPLE 15

The ethyl 9-methylsulphonamidocarbonylmethyl-4-oxo-4,5-dihydro-10H-imidazo[1,2-a]indeno[1,2-e]pyrazine-2-carboxylate can be obtained in the following manner: 2.34 g of ammonium acetate are added, with stirring, to a solution of 1.45 g of 2-(2,4-diethoxycarbonylimidazo-1-yl)-4-methylsulphonamidocarbonylmethylindan-1-one and 50 ml of acetic acid. The reaction medium is maintained at boiling temperature for 4 hours and then cooled and filtered on sintered glass. The solid residue is washed with twice 15 ml of acetic acid, twice 25 ml of water, 25 ml of acetone and dried under reduced pressure at 60° C. 0.8 g of ethyl 9-methylsulphonamidocarbonyl-methyl-4-oxo-4,5-dihydro-10H-imidazo[1,2-a]indeno[1,2-e]pyrazine-2-carboxylate is thus obtained in the form of a beige solid melting above 260° C. ($R_f$=0.38, thin-layer chromatography on silica gel, eluent: chloroform/methanol/ammonium hydroxide: 12/6/1).

The 9-methylsulphonamidocarbonylmethyl-4-oxo-4,5-dihydro-10H-imidazo[1,2-a]indeno[1,2-e]pyrazine-2-carboxylic acid can be obtained in the following manner: 4.4 ml of 1 N aqueous sodium hydroxide are added dropwise to a solution of 0.48 g of ethyl 9-methylsulphonamidocarbonylmethyl-4-oxo-4,5-dihydro-10H-imidazo[1,2-a]indeno[1,2-e]pyrazine-2-carboxylate, 45 ml of dioxane and 1.3 ml of distilled water. The reaction medium is kept stirring for 20 hours, filtered on sintered glass and the solid thus obtained is washed with twice 20 ml of dioxane, air-dried and then under reduced pressure at 60° C. 0.46 g of 9-methylsulphonamidocarbonylmethyl-4-oxo-4,5-dihydro-10H-imidazo[1,2-a]indeno[1,2-e]pyrazine-2-carboxylic acid is thus obtained as disodium salt in the form of a pink solid melting above 260° C. (Analysis: $C_{17}H_{12}N_4O_6S_1Na_2$, 6.21 $H_2O$, 0.49 $C_4H_8O_2$, % calculated C: 45.75, E: 2.71, N: 12.55, S: 7.18; % found C: 45.7, H: 2.3, N: 12.5, S: 7.2).

The 2-(2,4-diethoxycarbonylimidazol-1-yl)-4-methylsulphonamidocarbonylmethylindan-1-one can be obtained in the following manner: 1.61 g of 1,1'-carbonyldiimidazole are added in portions to a suspension of 2.6 g of diethyl 1-[4-(carboxymethyl)-1-oxoindan-2-yl]-imidazole-2,4-dicarboxylate in 65 ml of tetrahydrofuran and the reaction medium is kept stirring at a temperature close to 20° C. for 30 minutes and then at reflux for 30 minutes. After returning to a temperature close to 20° C., 0.61 g of methylsulphonamide is added to the reaction medium and ten minutes later a solution of 0.98 g of 1,8-diazabicyclo[5.4.0]undec-7-ene in 25 ml of tetrahydrofuran. The reaction medium is kept stirring for 18 hours and is then poured into 433 ml of 1 N hydrochloric acid. 220 ml of ethyl acetate are added to the solution obtained and the aqueous phase is extracted with 3 times 110 ml of ethyl acetate. The combined organic phases are washed with 110 ml of distilled water, dried over sodium sulphate, filtered on paper and concentrated under reduced pressure at 40° C. The solid residue thus obtained is purified by chromatography on silica with a dichloromethane-methanol (9-1 by volume) mixture as eluent. 1.45 g of 2-(2,4-diethoxycarbonylimidazol-1-yl)-4-methylsulphonamidocarbonylmethylindan-1-one are thus obtained in the form of a pink-grey foam melting at 139° C. (pasty).

The medicinal products according to the invention consist of a compound of formula (1) or a salt of such a compound, in the pure state or in the form of a composition in which it is combined with any other pharmaceutically compatible product, which may be inert or physiologically active. The medicinal products according to the invention may be used orally, parenterally, rectally or topically.

Tablets, pills, powders (gelatine capsules, cachets) or granules can be used as solid compositions for oral administration. In these compositions, the active ingredient according to the invention is mixed with one or more inert diluents such as starch, cellulose, sucrose, lactose or silica, under an argon stream. These compositions may also contain substances other than diluents, for example one or more lubricants such as magnesium stearate or talc, a colouring, a coating (sugar-coated tablets) or a glaze.

Pharmaceutically acceptable solutions, suspensions, emulsions, syrups and elixirs, containing inert diluents such as water, ethanol, glycerol, vegetable oils or paraffin oil, can be used as liquid compositions for oral administration. These compositiions may contain substances other than diluents, for example wetting, sweetening, thickening, flavouring or stabilizing products.

Sterile compositions for parenteral administration may be, preferably, aqueous or nonaqueous solutions, suspensions or emulsions. Water, propylene glycol, a polyethylene glycol, vegetable oils, in particular olive oil, injectable organic esters, for example ethyl oleate or other appropriate organic solvents may be used as solvent or vehicle. These compositions may also contain adjuvants, in particular wetting, isotonizing, emulsifying, dispersing and stabilizing agents. The sterilization can be performed in several ways, for example by asepticizing filtration by incorporating into the composition sterilizing agents, by irradiation or by heating. They can also be prepared in the form of sterile solid compositions which can be dissolved at the time of use in sterile water or any other injectable sterile medium.

Compositions for rectal administration are suppositories or rectal capsules which contain, in addition to the active product, excipients such as cocoa butter, semisynthetic glycerides or polyethylene glycols.

Compositions for topical administration may be for example creams, lotions, collyria, collutories, nasal drops or sprays.

In human therapy, the compositions according to the invention are particularly useful for the treatment and/or prevention of conditions which require the administration of an AMPA receptor antagonist or of an NMDA receptor antagonist. These compounds are especially useful for the treatment or prevention of all ischaemias and in particular cerebral ischaemia, the effects due to an anoxia, the progression of neurodegenerative diseases, of HUNTINGTON's chorea, of ALZHEIMER's disease and other dementias, of amyotrophic lateral sclerosis or of other motor neurone diseases, of olivopontocerebellar atrophy and of PARKINSON'S disease, against epileptogenic and/or convulsive manifestations, cerebral or spinal traumas, traumas linked to degeneration of the inner ear or of the retina, tinnitus, anxiety, depression, schizophrenia, TOURETTE's syndrome, hepatic encephalopathies, sleep disorders, attention-deficit disorders, hormonal-condition disorders (excess secretion of GH or LH, secretion of corticosterone), as analgesics, anti-inflammatories, antianoretics, antimigraines, antiemetics and for treating poisoning by neurotoxins or other substances which are NMDA or AMPA receptor agonists, as well as neurological disorders associated with viral diseases such as viral meningitis and encephalitis, AIDS, rabies, measles and tetanus, for the prevention of, tolerance of and dependency on drug and alcohol withdrawal symptoms and inhibition of acquired tolerance of and dependency on opiates, barbiturates, amphetamine and benzodiazepines, in the treatment of deficiencies linked to mitochondrial abnormalities such as mitochondrial myopathy, LEBER's syndrome, WERNICKE's encephalopathy, RETT's syndrome, homocysteinaemia, hyperprolinaemia, hydroxybutyric-aminoaciduria, saturnine encephalopathy (chronic lead poisoning) and sulphite oxidase deficiency.

The doses depend on the desired effect, the duration of the treatment and the route of administration used; they are generally between 10 mg and 100 mg per day orally, for an adult, with unit doses ranging from 5 mg to 50 mg of active substance.

Generally, the doctor will determine the appropriate dosage according to the age, weight and all other factors which are specific to the subject to be treated.

The following examples illustrate the compositions according to the invention:

EXAMPLE A

Gelatine capsules containing 50 mg doses of active product having the following composition are prepared according to the customary technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing 50 mg doses of active product having the following composition are prepared according to the customary technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerin, titanium oxide (72-3.5-24.5) qs 1 finished 245-mg coated tablet | |

EXAMPLE C

An injectable solution containing 10 mg of active product having the following composition is prepared:

| | |
|---|---|
| Compound of formula (I) | 10 mg |
| Benzoic acid | 80 mg |
| Benzyl alcohol | 0.06 ml |
| Sodium benzoate | 80 mg |
| 95% ethanol | 0.4 ml |
| Sodium hydroxide | 24 mg |
| Propylene glycol | 1.6 ml |
| Water qs | 4 ml |

We claim:

1. A compound of formula (I):

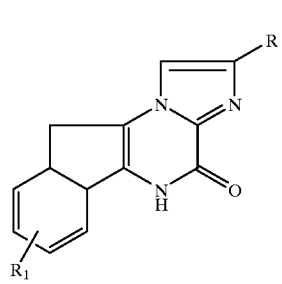

in which,

R represents a hydrogen atom or a —COOH radical, an -alk-COOH radical, a —PO$_3$H$_2$ radical, a —CH$_2$—PO$_3$H$_2$ radical, a —CH=CH—COOH radical or a phenyl radical substituted with a carboxyl radical, R$_1$ represents an -alk-CN, -alk-COOH, -alk-Het, -alk-PO$_3$H$_2$ or -alk-CO—NH—SO$_2$R$_2$ radical, R$^2$ represents an alkyl or phenyl radical, alk represents an alkyl radical, Het represents a saturated or unsaturated mono- or polycyclic heterocycle containing 1 to 9 carbon atoms and one or more heteroatoms selected from O, S, and N, the heterocycle being optionally substituted with one or more alkyl, phenyl or phenylalkyl radicals, with the proviso that when R represents a hydrogen atom or a —COOH or —PO₃H₂ radical, R₁ cannot represent -alk-COOH, and with the proviso that the alkyl radicals contain 1 to 6 carbon atoms in a straight or branched chain, an isomer, racemate, enantiomer, diastereoisomer, or a salt thereof.

2. A compound of formula (I) according to claim 1, wherein the substituent R₁ is at position 8 or 9.

3. A compound of formula (I) according to claim 1, wherein Het represents a tetrazol-5-yl ring.

4. A process for preparing a compound of formula (I) according to claim 1, said process comprising:

cyclizing, in the presence of ammonium acetate, ammonia, or ammonium acetate and ammonia, a compound of formula (II):

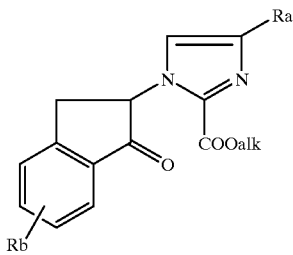

(II)

in which Ra represents a hydrogen atom or a —COOalk radical, an -alk-COOalk' radical, a —PO(Oalk)₂ radical, a —CH₂—PO(Oalk)₂ radical, a —CH═CH—COOalk' radical or a phenyl radical substituted with an alkoxycarbonyl radical, Rb represents an -alk-CN, -alk-COOalk', -alk-PO (Oalk')₂, -alk-CO—NH—SO₂R₂ or -alk-Het radical, alk and alk' each independently represent an alkyl radical, R₂ and Het have the same meanings recited for formula I in claim 1, with the proviso that when Ra represents a hydrogen atom, a —COOalk radical, or a —PO(Oalk)₂ radical, Rb cannot represent an -alk-COOalk' radical, hydrolyzing the product of said cyclization, isolating the product of said hydrolyzation, and optionally converting said isolated product into a salt.

5. A process for preparing a compound of formula (I) according to claim 1, said process comprising:

cyclizing, in the presence of ammonium acetate, ammonia, or ammonium acetate and ammonia, a compound of formula (II):

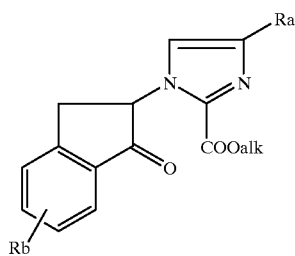

(II)

in which Ra represents a hydrogen atom or a —COOalk radical, an -alk-COOalk' radical, a —PO(Oalk)₂ radical, a —CH₂—PO(Oalk)₂ radical, a —CH═CH—COOalk' radical or a phenyl radical substituted with an alkoxycarbonyl radical, Rb represents an -alk-Het radical in which Het represents a tetrazolyl-5-yl radical in which the tetrazole is substituted at position 1 or 2 with a benzyl radical, debenzylating said cyclized compound, hydrolyzing said debenzylated product, isolating said hydrolyzed product, and optionally converting said isolated product into a salt.

6. A process for preparing a compound of formula (I) according to claim 1, wherein R represents an -alk-COOH radical in which alk is an alkyl radical containing 2 carbon atoms in a straight chain, said process comprising hydrogenating a compound of formula (I) in which R represents a —CH═CH—COOH radical, isolating said hydrogenated product, and optionally converting said isolated product into a salt.

7. A process for preparing a compound of formula (I) according to claim 1, wherein R represents a phenyl radical substituted with a carboxyl radial, said process comprising hydrolyzing a compound of formula (I) in which the phenyl radical is substituted with a cyano radical, isolating said hydrolyzed product, and optionally converting said isolated product to a salt.

8. A pharmaceutical composition, said composition comprising a pharmaceutically effective amount of at least one compound of formula (I) according to claim 1 and a pharmaceutically acceptable diluent.

9. A pharmaceutical composition, said composition comprising a pharmaceutically effective amount of at least one compound of formula (I) according to claim 2 and a pharmaceutically acceptable diluent.

10. A pharmaceutical composition, said composition comprising a pharmaceutically effective amount of at least one compound of formula (I) according to claim 3 and a pharmaceutically acceptable diluent.

* * * * *